United States Patent
Reddy et al.

(10) Patent No.: US 11,634,738 B2
(45) Date of Patent: Apr. 25, 2023

(54) USE OF MARINE ALGAE FOR CO-PRODUCING ALKENONES, ALKENONE DERIVATIVES, AND CO-PRODUCTS

(71) Applicants: Woods Hole Oceanographic Institution, Woods Hole, MA (US); Western Washington University, Bellingham, WA (US); Marine Biological Laboratory, Woods Hole, MA (US)

(72) Inventors: Christopher M. Reddy, Woods Hole, MA (US); Gregory W. O'Neil, Bellingham, WI (US); Scott R. Lindell, Woods Hole, MA (US)

(73) Assignees: Woods Hole Oceanographic Institution, Woods Hole, MA (US); Western Washington University, Bellingham, WA (US); Marine Biological Laboratory, Woods Hole, MA (US)

( * ) Notice: Subject to any disclaimer, the term of this patent is extended or adjusted under 35 U.S.C. 154(b) by 0 days.

(21) Appl. No.: 17/388,298

(22) Filed: Jul. 29, 2021

(65) Prior Publication Data
US 2021/0355512 A1 Nov. 18, 2021

Related U.S. Application Data

(60) Division of application No. 16/259,339, filed on Jan. 28, 2019, now Pat. No. 11,118,199, which is a
(Continued)

(51) Int. Cl.
*C12P 7/64* (2022.01)
*C12P 7/26* (2006.01)
(Continued)

(52) U.S. Cl.
CPC ............ *C12P 7/649* (2013.01); *C07D 303/32* (2013.01); *C10L 1/1802* (2013.01); *C10L 1/185* (2013.01);
(Continued)

(58) Field of Classification Search
CPC ..... C07C 49/00; C07D 303/32; C10L 1/1802; C10L 1/185; C10L 1/19;
(Continued)

(56) References Cited

U.S. PATENT DOCUMENTS

| 5,770,043 A | 6/1998 | Ellis et al. |
| 5,859,700 A | 1/1999 | Yang |

(Continued)

FOREIGN PATENT DOCUMENTS

| CN | 101368193 | 2/2009 |
| CN | 101368193 B | * 12/2010 |

(Continued)

OTHER PUBLICATIONS

Goepfert, "Microbial Biofuels: *Isochrysis* sp. and Phaedactylum Tricomium Lipid Characterization and Physiology Studies (thesis paper)", Carl von Ossielzky University, Oldenberg, Germany, Mar. 15, 2010 <http://www.whoi.edu/cms/files/Goepfert_ Master Thesis_ 60365.pdf>.

(Continued)

*Primary Examiner* — Ellen M McAvoy
*Assistant Examiner* — Chantel L Graham
(74) *Attorney, Agent, or Firm* — Douglas Denninger; Cristy Salanga

(57) ABSTRACT

A method comprising a series of selective extraction techniques for the parallel production of biodiesel and isolation of several valuable co-products including an alkenone hydrocarbon mixture of the kerosene/jet fuel range (primarily C10-, C12-, and C17-hydrocarbons) and fucoxanthin, a
(Continued)

high-valued carotenoid, from the marine alkenone-producing microalgae *Isochrysis*.

17 Claims, 17 Drawing Sheets

Related U.S. Application Data continuation of application No. 15/949,983, filed on Apr. 10, 2018, now Pat. No. 10,208,321, which is a division of application No. 14/599,460, filed on Jan. 17, 2015, now Pat. No. 9,970,034, which is a continuation-in-part of application No. 14/187,929, filed on Feb. 24, 2014, now abandoned, which is a continuation-in-part of application No. 13/298,576, filed on Nov. 17, 2011, now Pat. No. 9,879,288, which is a continuation-in-part of application No. 12/967,478, filed on Dec. 14, 2010, now abandoned.

(60) Provisional application No. 61/414,491, filed on Nov. 17, 2010, provisional application No. 61/287,585, filed on Dec. 17, 2009.

(51) Int. Cl.
| | | |
|---|---|---|
| *C07D 303/32* | (2006.01) | |
| *C12N 1/12* | (2006.01) | |
| *C10L 1/185* | (2006.01) | |
| *C10L 1/19* | (2006.01) | |
| *C10L 1/18* | (2006.01) | |
| *C12P 7/649* | (2022.01) | |
| *C11C 3/00* | (2006.01) | |
| *C07C 49/00* | (2006.01) | |

(52) U.S. Cl.
CPC .............. *C10L 1/19* (2013.01); *C12N 1/12* (2013.01); *C12P 7/26* (2013.01); *C07C 49/00* (2013.01); *C10L 2200/0476* (2013.01); *C10L 2200/0484* (2013.01); *C11C 3/003* (2013.01); *Y02E 50/10* (2013.01)

(58) Field of Classification Search
CPC ..... C10L 2200/0476; C10L 2200/0484; C11C 3/003; C12N 1/12; C12P 7/26; C12P 7/649; Y02E 50/10
See application file for complete search history.

(56) References Cited

U.S. PATENT DOCUMENTS

| | | | |
|---|---|---|---|
| 7,368,200 | B2 | 5/2008 | Zhu et al. |
| 7,476,705 | B2 | 1/2009 | Pajerski |
| 8,557,514 | B2 | 10/2013 | Bidle et al. |
| 9,879,288 | B2 | 1/2018 | Lindell et al. |
| 9,970,034 | B2 | 5/2018 | Reddy et al. |
| 10,208,321 | B2 | 2/2019 | Reddy et al. |
| 2005/0192388 | A1 | 9/2005 | Craun et al. |
| 2008/0155888 | A1 | 7/2008 | Vick |
| 2008/0260662 | A1 | 10/2008 | Johnsen |
| 2010/0170144 | A1 | 7/2010 | Day |
| 2011/0167714 | A1 | 7/2011 | Lindell et al. |
| 2012/0165490 | A1 | 6/2012 | Lindell et al. |
| 2013/0035532 | A1 | 2/2013 | Schrodi |
| 2014/0171608 | A1 | 6/2014 | Lindell et al. |

FOREIGN PATENT DOCUMENTS

| | | |
|---|---|---|
| ES | 2088366 | 8/1996 |
| WO | 2008079724 | 7/2008 |
| WO | 2009018230 | 2/2009 |

OTHER PUBLICATIONS

Christi et al., "Biodiesel from Microalgae", Biotechnology Advances, vol. 25, pp. 294-306, <http://linkinghub:elsevier.com/pii/s0734975007000262>.

Eltgroth et al., "Production an Cellular Localization of Long-Chain Neutral Lipids in the Haptophyte Algae Isochrysis Galbana and Emiliania Huxley", J. Phycol, 2005, 41, 1000-1009.

Haiduc et al., "An Integrated Process for Hydrothermal Production of Methane from Microalgae and CO2 Mitigation", J. Appl. Phycol., 2009, 21:529-541.

O'Neil et al., "Beyond Fatty Acid Methyl Esters: Expanding the Renewable Carbon Profile with Alkenones from Isochrysissp.", Energy Fuels, 26:2434-2441 (2012).

Stucki et al., "Cataltyic Gasification of Algae in Supercritical Water for Biofuel Production and Carbon Capture", Energy Environ. Sci., 2009, 2:535-541.

Sugawara et al., "Brown Algae Fucoxanthin is Hydrolyzed to Fucoxanthinol During Absorption by Caco-2 Human Intestinal Cells and Mice", J. Nutrition 132: 946-951, 2002.

Versteegh et al., "Uk'37 Values for Isochrysis Galbana as a Function of Culture Temperature, Light Intensity and Nutrient Concentralions", Organic Geochemistry, 2001, 32, 785-794.

Intonational Search Report for corresponding PCT/US2010/060259 dated Mar. 9, 2011.

Albentosa et al., "Evaluation of live microalgal diets for the seed culture of Ruditapes decussatus using physiological and biochemical parameters," Aquaculture, Dec. 10, 1996, vol. 148, Iss. 1, pp. 11-23.

Enright et al., "Evaluation of phytoplankton as diets for juvenile *Ostrea edulis* L.," Journal of Experimental Marine Biology and Ecology, Apr. 10, 1986, vol. 96, Iss. 1, pp. 1-13.

Inderwildi et al., "Quo vadis biofuels?," Energy & Environmental Science, Mar. 2009, vol. 2, Iss. 4, pp. 343-346.

Kaplan et al., "Algal Nutrition," Handbook of Microalgal Mass Culture, CRC Press, FL, 1986, pp. 147-198.

Lavens et al., "Manual on the production and use of live food for aquaculture," Food and Agriculture Organization of the United Nations, 1996, FAQ Fisheries Technical Paper 361, pp. 1-305.

Wikfors et al., "Ditferences in strains of Isochrysis of importance to mariculture," Aquaculture, Jun. 1, 1994, vol. 123, Iss. 1-2, pp. 127-135.

\* cited by examiner

|  | Fatty Acids | Alkenones | Botryococcenes |
|---|---|---|---|
| Algae Source | Various | E. hux., G. oceanica, Isochrysis | B. braunii |
| Carbon Number | Linear, 14 - 22 | Linear, 35 - 41 | Branched, 30 - 34 |
| Double Bonds | 0 - 6 methylene-interrupted cis-disubstituted alkenes | 1 - 3 trans disubstituted separated by 5 methylenes | 6 mono-, di-, and tri-substituted separated by 2-3 carbons |
| Heteroatoms | Carboxylic acid | Methyl or ethyl ketone | None |

FIG. 14

| Entry[A] | Catalyst | Solvent, 2-butene | Time | % Conversion[B] |
|---|---|---|---|---|
| 1 | Ru-HG | DCM, cis-butene | 18 h | 100 |
| 2 | Ru-HG | DCM, trans-butene | 18 h | 100 |
| 3 | Ru-II | DCM, cis-butene | 18 h | 100 |
| 4 | Ru-I | DCM, cis-butene | 18 h | 70.0 |
| 5 | Ru-HG | DCM, cis-butene | 3 h | 100 |
| 6 | Ru-HG | DCM, cis-butene | 1 h | 100 |
| 7 | Ru-HG | DCM, trans-butene | 1 h | 100 |
| 8 | Ru-HG | DCM | 10 min | 62.9 |
| 9 | Ru-HG | DCM | 20 min | 98.8 |
| 10 | Ru-HG | DCM | 30 min | 99.5 |
| 11 | Ru-I | DCM | 3 h | 9.5 |
| 12 | Ru-I | DCM | 6 h | 16.7 |
| 13 | Ru-HG | PhMe | 10 min | 52.5 |
| 14 | Ru-HG | PhMe | 20 min | 84.4 |
| 15 | Ru-HG | PhMe | 30 min | 98.3 |
| 16 | Ru-HG | DCM/trans-butene | 15 min | 37.4 |
| 17 | Ru-HG | DCM/trans-butene | 30 min | 95.5 |

*Footnote for Table 2:* [A]All reactions were performed by adding alkenones (100 mg) to condensed 2-butene (15 equiv.) at -78 °C followed by solvent (1 mL) and catalyst. The flask was then sealed and placed in a refrigerator (4 °C, Entries 1-7) or ice bath (0 °C, Entries 8-17) for the indicated time before quenching with ethyl vinyl ether (50 equiv.) and concentrating *in vacuo*. [B]Percent conversions were calculated by GC-FID for the combined alkenone signals relative to methyl stearate as an inert internal standard pre- and post-butenolysis. For those reactions reported as 100% conversion, no alkenone signal was detectable by GC-FID.

FIG. 15

| Alkenones (double bond position)[A] | % Composition[B] This Study | % Composition[C] Ref 54 | Predicted Butenolysis Products (%)[D] |
|---|---|---|---|
| Me 37:3 (8E,15E,22E) | 42 | 40 | 1 (12.4), 2 (28.2), 3 (42.7), 15-heptadecen-2-one (8.0), 9-undecen-3-one (1.4), 16-octadecen-3-one (6.6), 2-nonadecene (0.7) |
| Me 37:2 (15E,22E) | 27 | 29 | |
| Et 38:3 (9E,16E,23E) | 5 | 6 | |
| Et 38:2 (9E,16E,23E) | 23 | 22 | |
| Me 39:3 (8E,15E,22E) | 1 | ND | |
| Me 39:2 (15E,22E) | 2 | ND | |

*Footnotes for Table 3:* [A]Double bond positions are based on information in references 51-53. [B]Determined by GC-FID and calculated as percent of total alkenones. [C]Average values for T-Iso and C-Iso from reference 54. [D]Percent of total predicted products. ND = not determined.

FIG. 16

| Isochrysis DW (g) | 30.0 | 50.6 |
|---|---|---|
| Biofuel Oil (g) | 5.86 | 8.09 |
| Biomass Oil (g) | 2.18 | 2.22 (24 h)[B] <br> 0.97 (1 h)[B] |
| Biomass Oil Fucoxanthin Content (mg/g)[A] | 0.189 | 0.215 (24 h)[B] <br> 0.200 (1 h)[B] |
| Biofuel Oil Fucoxanthin Content (mg/g)[A] | 0.032* | 0.029* |

FIG. 17

USE OF MARINE ALGAE FOR CO-PRODUCING ALKENONES, ALKENONE DERIVATIVES, AND CO-PRODUCTS

CROSS-REFERENCE(S) TO RELATED APPLICATIONS

This application is a divisional of U.S. application Ser. No. 16/259,339, filed Jan. 28, 2019, which is a continuation of U.S. application Ser. No. 15/949,983, filed Apr. 10, 2018, now allowed, which is a divisional of U.S. application Ser. No. 14/599,460, filed Jan. 17, 2015, now U.S. Pat. No. 9,970,034, issued May 15, 2018, which is a continuation-in-part of U.S. application Ser. No. 14/187,929, filed Feb. 24, 2014, abandoned, which is a continuation-in-part of U.S. application Ser. No. 13/298,576, filed Nov. 17, 2011, now U.S. Pat. No. 9,879,288, issued Jan. 30, 2018, which is a continuation-in-part of U.S. application Ser. No. 12/967,478, filed Dec. 14, 2010, abandoned, and claims benefit of U.S. Provisional Application Ser. No. 61/414,491, filed Nov. 17, 2010; and U.S. Provisional Application Ser. No. 61/287,585, filed Dec. 17, 2009. The entire contents of each of the above referenced applications are incorporated herein by reference in their entireties and without disclaimer.

STATEMENT OF GOVERNMENT LICENSE RIGHTS

This invention was supported in part by the United States Government under National Science Foundation Grant No. CHE-1151492, and in part by the State of Massachusetts under Massachusetts Clean Energy Center Grant No. 16489900. The government has certain rights in the invention.

FIELD OF THE INVENTION

The present invention describes improved methods and extraction techniques for the parallel production of biodiesel, alkenones, alkenone derivatives including an alkenone hydrocarbon mixture of the kerosene/jet fuel range (primarily C10-, C12-, and C17-hydrocarbons), and isolation of valuable co-products including fucoxanthin, a high-valued carotenoid, from marine algae.

BACKGROUND OF THE INVENTION

Increased global demand and consumption of easily accessible petroleum and natural fossil fuels continue to be unpredictable in future prices and put a constant pressure on economies, politics, and importantly, the environment. These pressing issues have led to a growing need for alternative, renewable, and sustainable energy sources and additional developments in production of alternative fuels.

Currently, the largest volume of renewable fuel sources or biofuels is derived from agricultural feedstocks including plant-based sugars and oils (i.e. carbohydrates and acylglycerols, respectively) and other derivatives. However, reliance on edible crop-based fuels is not a long-term energy solution since premium farmland, abundance of water, and energy are in limited supply. Therefore, it is beneficial to seek out additional sources for biofuels and efficient methods of production.

In recent years, potential biofuel sources such as algae have shown to be promising alternatives to crop-based biofuels. Advances in cultivation, processing, and production have demonstrated not only the feasibility of using algal sources in terms of cost, labor, and time, but also the potential value in parallel production of commercially useful co-products.

Algae can produce 10 to 100 times as much mass as terrestrial plants in a year. Algae also produce oils (lipids) and starches that may be converted into biofuels. Algae useful for biofuel production include algae known as microalgae, consisting of small, often unicellular, types. These algae can grow almost anywhere, though most are commonly found at latitudes between 40 N and 40 S. With more than 100,000 known species of diatoms (a type of algae), 40,000 known species of green plant-like algae, and smaller numbers of other algae species, algae will grow rapidly in nearly any environment, with almost any kind of water, including marginal areas with limited or poor-quality water.

While the cost of petroleum has increased dramatically in recent years, critics remain who contend that nonetheless algal biofuels will prove too costly to manufacture on a larger scale, and that algae productivities do not surpass those of irrigated crops and cultivating, harvesting, and processing microalgae is simply too expensive. Adding the production of both supplementary biofuels and valuable co-products can make energy production using algae commercially viable and a key reason to further explore algae as a biofuel source.

The most notable product yielded from algal biofuel production is biodiesel in the form of long-chain alkyl esters and more specifically, fatty acid methyl esters (FAMEs). However, another unique and promising class of algal compounds known as long-chain alkenones (e.g. alkenones) are naturally biosynthesized by certain species of algae, namely members of the *Isochrysis*, *Emiliania*, and the *Gephyrocapsa* families, in parallel to compounds required for biodiesel production. Alkenones may be converted to smaller hydrocarbon fragments in the range of jet fuel and kerosene through a separate processing method than utilized for biodiesel/FAME synthesis. Thus, jet fuel-range biofuels may be produced in parallel with biodiesel from a single batch of algae, adding another level of commercial value.

Additionally, from this single batch of algae, it is possible to simultaneously isolate other valuable co-products such as fucoxanthin, astaxanthin, beta-carotene, and other carotenoids. Fucoxanthin, in particular, has been reported for health benefits as an antioxidant, anti-inflammatory, anti-cancer chemical with industrial uses as well. Therefore, there is an unmet need and desire to use algae not only as a diversified source of biodiesel which does not rely on food resources, but as an economically viable source of biodiesel, biofuel, and additional desirable co-products.

SUMMARY

In accordance with the present invention, parallel methods are provided for producing alkenone derivatives and commercially valuable co-products from algae. In one aspect, the disclosure provides a method which comprises: (a) culturing an alkenone-producing alga under a growth condition sufficient to produce alkenones within the alga; (b) separating the biofuel oil comprising the alkenones from the biomass comprising the valuable co-products; (c) isolating the alkenones from the biofuel oil; (d) chemically modifying the alkenones to produce alkenone derivatives of a hydrocarbon length in the range of liquid transportation fuels (e.g. jet fuel, kerosene); and (e) chemically modifying the biomass to produce co-products.

In certain embodiments, the alkenone-producing alga is a species of the *Isochrysis* family, such as *Isochrysis* galbana, *Isochrysis* sp. T-iso, and *Isochrysis* sp. C-iso. The alkenones of the alga may comprise alkenones having a number of carbons ranging from 30 to 42. The alkenones may be converted to alkenone derivatives by a cross metathesis reaction. In certain embodiments, the alkenones are processed into a liquid fuel such as diesel and gasoline. In other embodiments, the alkenones are processed into a gaseous fuel, such as a syngas (a mixture of CO and H2) and/or a synthetic hydrocarbon gas (e.g. methane, propane, and butane). In certain embodiments, the alga also produces fatty acids and by-products (e.g. acylglycerols). Optionally, the method comprises converting a mixture of fatty acid compounds and alkenones to products (e.g. alkenone derivatives, FAMEs, etc.) without separating the fatty acid compounds from the alkenones. In certain embodiments, the growth condition for culturing the alga may include a stationary growth phase, a high temperature, sufficient light, nutrient limitation or a combination thereof. In certain specific embodiments, algae are directly converted into methane via hydrothermal gasification.

Additionally, the waste-stream (i.e. the biomass) normally discarded in the production of biodiesel and alkenone derivatives may be processed to produce co-products with a monetary value without alteration of the algae-to-biodiesel/algae-to-alkenone derivatives processes. In one embodiment, the isolated biomass is extracted to produce valuable carotenoids such as fucoxanthin.

Optionally, growing of algae and hydrothermal processing of algae biomass are coupled into a continuous process. In certain embodiments, chemically modifying the alkenones comprises pyrolyzing or cracking the alkenones. In some embodiments, alkenone derivatives of step (b) are acrylic acids, acrylic esters, alkenes, vinyl chloride, vinyl acetate, diacids, diamines, diols, or lactic acid.

In certain aspects, the disclosure provides modified algal strains which may enhance the products derived from the claimed methods.

DESCRIPTION OF THE DRAWINGS

FIG. 14 shows comparison of fatty acid, alkenone, and botryococcene structures for consideration as a biofuel feedstock.

FIG. 15 shows results from butenolysis reactions 11 of alkenone mixtures 9 isolated from *Isochrysis*.

FIG. 16 shows alkenone composition 9 and expected butenolysis products 12.

FIG. 17 shows yields and fucoxanthin content 16 for the biofuel oil 4 and the biomass oil 3 obtained by sequential hexanes/ethanol extraction 2 of dry *Isochrysis* algae culture 1.

DETAILED DESCRIPTION

Figure 1:
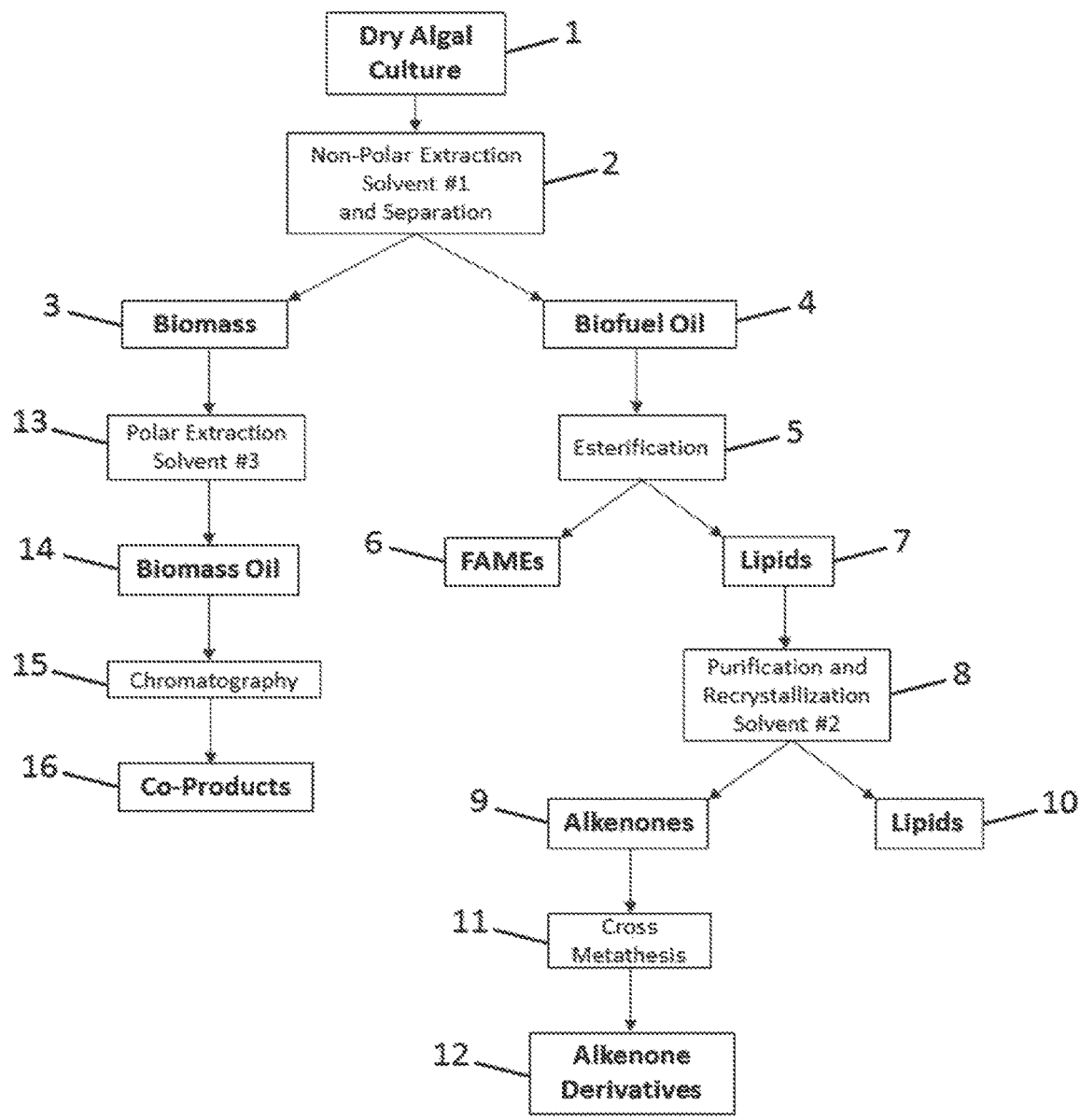
FIG. 1 shows a schematic of the co-production processes of alkenones 9, alkenone derivatives 12, and co-products 16.

The present invention provides parallel methods for co-producing alkenones and alkenone-derivatives suitable for use as biofuel, in particular jet fuel and/or kerosene and valuable co-products from a single batch of algae.

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

Throughout this specification, the word "comprise" or variations such as "comprises" or "comprising" will be understood to imply the inclusion of a stated integer or groups of integers but not the exclusion of any other integer or group of integers.

The singular forms "a," "an," and "the" include the plurals unless the context clearly dictates otherwise.

The term "including" is used to mean "including but not limited to." "Including" and "including but not limited to" are used interchangeably.

The term "substantially pure" as used herein refers to a chemical that is chemically pure or analytically pure—this the chemical has a purity greater than 70%, greater than 75%, greater than 80%, greater than 85%, greater than 90%, greater than 95%, greater than 8%, or greater than 99%.

The term "co-product" means a product that is prepared in the presence of another product.

The term "commercially useful product" is used to define a product of which has monetary value and/or economic demand.

The term "polar solvent" refers to a solvent wherein there is either a permanent separation of positive and negative charges, or the centers of positive and negative charges do not coincide, in the molecules. Polar solvents include, but are not limited to chloromethane, dichloromethane, dichloroethane, tetrahydrofuran, dimethylformamide, acetonitrile, nitromethane, propylene carbonate, formic acid, butanol, isopropanol, methyltetrahydrofuran, trifluoromethylbenzene, ethyl acetate, ethyl ether, acetone, dimethyl sulfoxide, alcohols, acetic acid, and esters. In some embodiments, the polar solvent is selected from the group of dichloromethane, dichloroethane, tetrahydrofuran, methyltetrahydrofuran, ethanol, and other alcohols.

The term "non-polar solvent" refers either to a solvent without significant partial charges on any atoms (e.g. hydrocarbons) or to a solvent in which the polar bonds are arranged in such a way that the effects of their partial charges are cancelled out (e.g. chloroform). Non-polar solvents include, but are not limited to, hydrocarbons containing 1 to 22 carbons, benzene, toluene, xylene, pentane, cyclohexane, n-heptane, n-hexanes, octane, iso-octane, chloroform, ether, dimethyl ether, diethyl ether, methyl-tert-butyl ether, 1,4-dioxane, and neutral or non-ionic surfactants. In some embodiments, the non-polar solvent is selected from n-hexanes, iso-hexane, n-heptane, and iso-heptane.

The term "more polar than hexane" refers to a solvent with a greater separation in electromagnetic charges between atoms than hexanes wherein hexane consists of equal sharing of electromagnetic charge between atoms. Solvents more polar than hexane include but are not limited to ethanol, methanol, chloromethane, dichloromethane, dichloroethane, tetrahydrofuran, methyltetrahydrofuran, ethyl acetate, acetone, dimethyl sulfoxide, alcohols, acetic acid, esters, ketones, amines, carboxylates, and halogenated hydrocarbons.

The term "biofuel oil" refers to the extracted oil obtained from the extraction with solvent #1 comprising a fatty acid-rich fraction (e.g. fatty acids, fatty acid derivatives) and a lipid-rich fraction (e.g. lipids, alkenones).

The term "biomass oil" refers to the extracted oil obtained from the extraction of the algal biomass with solvent #3 of which comprises co-products.

The term "biomass" or "algal biomass" refers to the algal cellular debris (e.g. cellular residue, enzymes, by-products, etc.) removed of the biofuel oil obtained by extraction with solvent #1.

The term "alkenone derivatives" refers to the products derived from alkenones or chemical modification of alkenones.

The term "minimal amount of light" refers to the minimal amount of time which the reaction, reagents, products, etc. (e.g., the reaction mixture) are in the presence of light. In some embodiments, the term "minimal amount of light" is exposure of 0 seconds, exposure of less than 5 seconds, exposure of less than 10 seconds, exposure of less than 15 seconds, exposure of less than 30 seconds, exposure of less than 1 minute, exposure of less than 2 minutes, exposure of less than 3 minutes, exposure of less than 4 minutes, exposure of less than 5 minutes, exposure of less than 6 minutes, exposure of less than 7 minutes, exposure of less than 8 minutes, exposure of less than 9 minutes, or exposure of less than 10 minutes.

The term "alkenone-enriched sample" refers to a sample comprising alkenones and lipids.

The term "non-alkenone containing sample" refers to a sample obtained from the aqueous phase of the 2-phase mixture of the polar extraction of the algal culture which may be the waste-stream discarded in the production of biodiesel.

The term "alkenone-enriched phase" refers to the first polar phase (e.g. polar phase) of the two-phase system of the algae extraction which comprises lipids and alkenones.

The term "commercially valuable second molecule" or "commercially valuable second product" refers to at least one product obtained from second phase of the two-phase system of the algae extraction.

Algae Species as a Feedstock and Alkenone Source

Algae can store energy in the form of either oil or starch. Stored oil can be as much as 60% of the weight of the algae. Certain species which are highly prolific in oil or starch production have been identified, and growing conditions have been tested. Processes for extracting and converting these materials to fuels have also been developed. As referred herein, the terms "lipids" and "oil" are used interchangeably. Additionally, reference to "lipids" also includes "alkenones".

In certain embodiments, the subject methods make use of certain species of algae which are capable of producing lipids. In a specific embodiment, the subject methods employ algae species which produce alkenones, a class of lipids. Alkenes, alkenoates, and other polyunsaturated long-chain alkenones (PULCA), typically comprise 35 to 40 carbons and methyl or ethyl ketones, although 37 and 38 carbons are generally the most dominant. Certain algae species (e.g. *Isochrysis* galbana, *Isochrysis* litoralis, *Isochrysis maritima*, *Emiliania huxleyi*, and *Gephyrocapsa oceanica*) produce PULCA and package them into cytoplasmic vesicles or lipid bodies. The amount of these lipid bodies may change in response to various growth conditions. For example, these lipid bodies may increase under nutrient limitation, stationary phase, light changes, or temperature changes. On the other hand, these lipid bodies may decrease under prolonged darkness or too low temperatures.

Lipid-producing algae can include a wide variety of algae. The most common lipid-producing algae can generally include, or consist essentially of, haptophytes (prymnesiophytes), diatoms (bacillariophytes), green algae (chlorophytes), blue-green algae (cyanophytes), and golden-brown algae (chrysophytes). Specific non-limiting examples of haptophytes include *Isochrysis, Pleurochrysis, Coccolithus, Chrysochromulina, Prymnesium, Chrysotlla, Dicrateria, Emiliania*, and *Gephyrocapsa*. Specific non-limiting examples of bacillariophytes capable of lipid production include the genera *Amphipleura, Amphora, Chaetoceros, Cyclotella, Cymbella, Fragllaria, Hantzschia, Navicula, Nitzschia, Phaeodactylum*, and *Thalassiosira*. Specific non-limiting examples of chlorophytes capable of lipid production include *Ankistrodesmus, Botryococcus, Chlorella, Chlorococcum, Dunaliella, Monoraphidium, Oocystis, Scenedesmus*, and *Tetraselmis*. In one aspect, the chlorophytes can be *Chlorella* or *Dunaliella*. Specific non-limiting examples of cyanophytes capable of lipid production include *Oscillatoria* and *Synechococcus*. A specific example of chrysophytes capable of lipid production includes *Boekelovia*.

In some embodiments, the subject methods employ an alkenone-producing alga, for example, a species of Haptophyceae and a member of the class of Prymnesiophyceae, the *Isochrysis* family, which includes, but is not limited to,

*Isochrysis* litoralis, *Isochrysis* maritima, *Isochrysis* galbana, *Isochrysis* sp. T-Iso, and *Isochrysis* sp. C-Iso. Other examples of alkenone-producing algae from the *Emiliania* family and the *Gephyrocapsa* family include *Emiliania huxleyi* and *Gephyrocapsa oceanica*. For the co-production of biodiesel, alkenone-derived biofuels, and biomass-derived co-products, many of species of algae such as Odontella are not appropriate as alkenones are only naturally produced in the Prymnesiophyceae class of algae species. Other species would require genetic manipulation to induce the production of alkenones which may be considered and employed by the inventive methods.

In certain aspects, the lipid-producing algae (e.g. alkenone-producing algae) can have a lipid content greater than about 20%, and preferably greater than about 30% by weight of the algae. Currently known species contain a practical maximum lipid content of about 40% by weight, although levels as high as 60% have been shown, and strains developed or discovered in the future may achieve practical maximums higher than 40%. Such species would certainly be useful in connection with the present invention. In some embodiments, the subject methods are used to measure alkenone content of alkenone-containing species in order to select for new algae species capable of producing high levels of lipids (e.g. alkenones). In some embodiments, the content of lipids is at least 20%, at least 30%, at least 40%, at least 50%, at least 60%, at least 70%, at least 80%, or at least 90% by weight of the algae.

In some embodiments, the alkenone-producing algae contain at least 3% alkenones 9 (w/w) relative to the starting dry algal culture 1. In another embodiment, the alkenone-producing algae comprises at least 5%, at least 7%, at least 10%, or even at least 20% alkenones 9 (w/w) relative to the starting dry culture 1. In one embodiment, an alkenone-producing algal species is produced by in vitro or in vivo selection and contains at least 5% alkenones by weight. In some embodiments, the concentrations of alkenones 9 contained in the lipid-rich fraction 7 is at least 10%, at least 20%, at least 30%, at least 40%, at least 50%, at least 60%, or at least 80% (w/w).

In certain aspects, the subject methods may include a combination of an effective amount of two or more algae species in order to maximize benefits (e.g. achieving optimal production of lipids including alkenones).

In other aspects, the subject methods are directed towards a particular algae species, while foreign species are preferably minimized and kept below an amount which would detrimentally affect yields of desired lipids (e.g. alkenones). Undesirable algae species can be controlled and/or eliminated using any number of techniques. For example, careful control of the growth environment can reduce introduction of foreign species. Alternatively, or in addition to other techniques, a virus selectively chosen to specifically target only the foreign species can be introduced into the growth reservoirs in an amount which is effective to reduce and/or eliminate the foreign species. An appropriate virus can be readily identified using conventional techniques. For example, a sample of the foreign algae will most often include small amounts of a virus which targets the foreign algae. This virus can be isolated and grown in order to produce amounts which would effectively control or eliminate the foreign algae population among the more desirable lipid-producing algae.

In other embodiments, lipid-producing algae may be virally infected to benefit the outcome and isolation of specific compounds such as alkenones 9 or co-products 16 (i.e. products derived from the biomass) derived from the inventive methods. The host algae may be induced by the viral components to serve as a platform for producing desired compounds. In some embodiments, the lipid or other compound composition changes over the course of infection. Such a viral infection may be employed to alter the alkenone unsaturation profile or to ultimately fine-tune the alkenone derivatives 12 obtained in the subject methods. In other cases, the viral infection may increase one or more types of lipids 7 and/or alkenones 9 to boost extraction yields. In another case, the viral infection reduces undesired compounds which may reduce extraction yields.

In other embodiments with respect Bidle et al. U.S. Pat. No. 8,557,514 incorporated by reference, the viral infection inhibits apoptotic pathways to increase lipids to produce higher yields of alkenones 9 and thus their subsequent derivatives 12. Other embodiments increase production of carotenoids and/or additional co-products 16 that may be isolated through the biomass isolation process 13 in response to viral infection. Furthermore, in other embodiments, the virally-infected algae is induced to undergo apoptosis to release the cellular contents (e.g. lipids 7, alkenones 9, carotenoids, co-products 16, etc.), allowing the extraction processes to proceed more efficiently.

In some embodiments, the algae has been modified to alter the composition of desired compounds or traits thereof by chemical or genetic manipulation (e.g. drug treatment, recombinant DNA, genetic engineering, transgenes, gene knockdown/knockout, nuclear transformation, gene transfer via bacteria, electroporation) such as lipid content, alkenone content, carotenoid content, fucoxanthin content, photosynthetic rate, growth rate, gene expression, protein expression, etc. as a means to create a strain or strains capable of producing high levels of these desired compounds. In some embodiments, an alga strain is genetically modified to produce a higher lipid and/or alkenone content than an unmodified strain, resulting in an alkenone-enriched strain.

In some embodiments, genetic material is introduced into a strain of algae to increase lipid and alkenone levels. The alga strain is transfected with a plasmid or plasmids containing constitutively active promoters, transcription factors (e.g. VP16), or possibly enhancer regions that drive and increase the gene expression and protein levels of other genes involved in the production, use, and/or storage of lipids, alkenones, fatty acids, or other desired algae compounds. Non-limiting examples of promoters that may be used are the Rubisco small subunit (RbcS2), ubiquitin (Ubi1), cauliflower mosaic virus (CaMV35S), Cytomegalovirus (CMV), modified Cytomegalovirus enhancer with the beta-actin promoter (CAG), and simian virus 40 (SV40). In another embodiment, the alga strain is transfected with a plasmid or plasmids containing constitutively repressive promoters or transcription factors (e.g. Engrailed) that decrease the gene expression and protein levels of other genes involved in the production, use, and/or storage of lipids, alkenones, fatty acids, or other desired algae compounds. Genes of interest may include, but are not limited to, enzymes involved in lipid biosynthesis, fatty acid modifying genes (e.g. desaturases, thioesterases), energy utilization genes, etc. In a particular embodiment an alkenone-rich algal species is transfected with one or more genes providing resistance to a toxin (e.g. antibiotic or antiviral), and the entire culture population is exposed to the toxin resulting in a highly enriched alkenone-producing algal population. In another embodiment, alkenone-producing cells are transfected with a reporter gene (e.g. green fluorescent protein) linked to a promoter for a marker of enzyme or protein expression important in alkenone synthesis or metabolism, to identify cells producing high levels of alkenones. Useful such promoters include the promoters for fatty acid unsaturase, fatty acid synthetase, acetyl-CoA carboxylase, glucokinase, pyruvate kinase, glycerol-3-phosphate acyltransferase, triacylglycerol lipase, monoacylglycerol lipase, as well as other synthetases, carboxylases, acyltransferases, dehydrogenases, lipases, and kinases associated with fatty acid or lipid synthesis or enhancer regions of said genes.

In other embodiments, a transgenic alga strain (i.e. strain with exogenous genetic material incorporated into the endogenous alga genetic material) is developed. In additional embodiments, the transgenic alga strain is further modified by the transfection of plasmids to create strains capable of producing even higher levels of the desired compounds. In some embodiment, nuclear transformation, gene transfer, or electroporation is utilized to incorporate transgenes into alga strain genome.

In other embodiments, specific genes are knocked out or knocked down (i.e. no or reduced gene expression) using genome editing techniques (i.e. TALENs (transcription activator-like effector nucleases), CRISPR/Cas (clustered regularly interspaced short palindromic repeats/CRISPR-associated genes), morpholinos, antisense oligos). One case uses TALENs to directly target the gene or genes of interest; another case utilizes the CRISPR/Cas gene editing technique to target the gene or genes of interest. Suitable targets for reduction of expression include but are not limited to, lipid storage genes, lipid degradation genes, etc. In one embodiment, a lipase (a lipid-reducing enzyme) gene is knocked out or gene expression is reduced to allow increased storage of lipids, alkenones, fatty acids, and/or other biofuel relevant compounds.

The algae may also be identified and selected for desired traits manually without the introduction of genetic material. In some embodiments, the alga strain is screened and selected for higher levels of compounds (e.g. lipids, alkenone, carotenoids, fucoxanthin, etc.) than naturally present in algae without selection. In other embodiments, the algae are subjected to exposure of drugs, mutagens, or other chemicals to alter the lipid, alkenone, and/or co-product contents.

Culturing Algae

In accordance with the present invention, the algae can be grown in reactors or reservoir structures, such as ponds, troughs, vats, or tubes, which are protected from the external environment and have controlled temperatures, atmospheres, and other conditions. Optionally, algae growth reservoirs can include a carbon dioxide source and a circulating mechanism configured to circulate alkenone-producing algae within the algae growth reservoirs. One way to achieve large surface growth areas is in large ponds or in a captive marine environment. In one embodiment, a raceway pond can be used as an algae growth reservoir in which the algae is grown in shallow circulating ponds with constant movement around the raceway and constant extraction or skimming off of mature algae. Other examples of growth environments or reservoirs include bioreactors.

It is also known that certain species of algae are much more prolific in the production of lipids than others. However, these species may be susceptible to predation or displacement by native or volunteer species which exist naturally in the environment where the growth reservoir is located. Moreover, in most locations, temperatures may reach extremes of heat or cold which could damage or at least retard the growth of the algae. As such, some form of protection is usually desirable for the chosen algae species. In certain embodiments, low-cost greenhouses can be built over the raceway ponds. These greenhouses can have enough integrity to maintain a positive pressure with airlocks, filtration, and temperature control. This integrity can prevent the entrance of wild algae and can maintain desired conditions for the algae crop.

In certain embodiments, the subject methods contemplate culturing an alkenone-producing alga under a growth condition sufficient to produce alkenones within the alga. Optionally, the growth conditions for culturing the alga may include growing the alga in a stationary growth phase, growing the alga under a high or low temperature, growing the alga in the presence of sufficient light (e.g. sunlight, artificial light, dim light, low light intensity, high light intensity, light >12 hr/day), growing the alga under a stress, or a combination thereof. Non-limiting examples of suitable stress include nutrient deprivation (e.g. nitrogen, phosphorous, and/or silicon), injection of a reactive oxygen source (e.g. ozone or peroxide), viral, bacterial, or fungal infection, and/or chemical additives. The underlying theory is that the algae, under stress, store up energy in the compact form of lipids and alkenones by extracting carbon and energy from the available nutrients in preparation for possible long-term harsh conditions. In some embodiments, algae are deprived of nitrogen, phosphorus, silicon, or a combination of the three nutrients to increase the biosynthesis of lipids, fatty acids, and alkenones of 5%, 10%, 20%, 30%, 40%, 50%, and up to 80%.

In one embodiment, the algae are cultured in greenhouse ponds under sufficient lighting (e.g. natural sunlight, artificial light, dim light) in a culture medium of suitable quality, including nutrients, pH, salinity, and other chemical parameters, such as a modified F/2 media or similar media known to those in the art. The algae are often grown in temperatures ranging $10°$ C. to over $55°$ C., with optimal conditions near $18°$ C. to $25°$ C. In some embodiments, the algae are grown in temperatures lower than $25°$ C., $20°$ C., $15°$ C., $10°$ C., or even less than $5°$ C. as a means to increase and/or alter the lipid content of the algae and to produce higher levels of less saturated lipids (e.g. lipids, alkenones) wherein the less saturated lipids are used to produce alkenone derivatives of a carbon number of 5 to 20. In other embodiments, the algae are grown in temperatures greater than $10°$ C., greater than $15°$ C., greater than $20°$ C., greater than $25°$ C., greater than $30°$ C., greater than $35°$ C., and sometimes greater than $55°$ C. to produce more saturated lipids (e.g. lipids, alkenones) wherein the more saturated lipids are used to produce alkenone derivatives containing 5 to 20 carbon atoms. In some embodiments, the algae are grown in temperatures greater than $10°$ C., greater than $15°$ C., greater than $20°$ C., greater than $25°$ C., greater than $30°$ C., greater than $35°$ C., greater than $40°$ C., greater than $45°$ C., greater than $50°$ C. or greater than $55°$ C.

In other embodiments, the algae are subjected to low light conditions (i.e. 2 to 15 $\mu$mol photons $m^{-2} s^{-1}$) to increase specific lipid contents. In other embodiments, the algae are subjected to high light conditions (i.e. 15 up to 135 $\mu$mol photons $m^{-2} s^{-1}$) to increase specific lipid contents. In some cases, the algae are grown in continuous light; in other cases, the algae are grown under 12 h/12 h light and dark cycle as a means to produce higher levels of lipids. Additionally, the light and dark cycle may be changed to 14 h/10 h, 16 h/8 h, 18 h/6 h, respectively.

In other embodiments, the algae are obtained from a mariculture facility. Industrially farmed algae may provide the scale necessary to produce biofuel as promising sources of alternative energy and valuable co-products.

Harvesting Algae

Algae may be harvested in multiple ways. In one approach, algae are harvested by concentration (e.g. filtration) and dehydration. In a specific embodiment, a lyophilized (e.g. freeze-dried) algal sample is obtained for further processing as described below. Other embodiments, the algae is dried or dehydrated by evaporation with or without the addition of solvents by vacuum drying, drum drying, hot air exposure (e.g. convective or direct drying), dielectric drying, supercritical drying, natural air drying, or other suitable method to produce a sample removed of fluid (e.g. non-aqueous sample) to produce the dry culture 1. In other embodiments, a wet algal biomass sample is processed. Furthermore, the algal sample may be lysed, crushed, or ground, either prior or subsequent to dehydration, although various embodiments do not require the algal sample to be in the powder form. Additionally, the crushing of algae using a high-pressured method of homogenizing the culture sample may not be appropriate for the production of biodiesel 6 and biofuel 12 in parallel with the production of co-products 16 from the biomass 3.

Recovery of Lipids from the Algae

The subject methods relate to recovery of lipids (e.g. alkenones) from the algae. Algae store lipids inside the cell body, sometimes but not always, in vesicles. The lipids can be recovered in various ways, including through the use of solvent extractions, either alone or in the presence of heat, pressure, and/or depolymerization processes (such as biologically breaking the walls of the algal cell and/or oil vesicles, if present, to release the lipids from the algae). In certain embodiments, at least one of three types of biological agents may be used to release algae energy stores, for example, enzymes such as cellulase or glycoproteinase, structured enzyme arrays, or a system such as a cellulosome, a viral agent, or a combination thereof. A cellulase is an enzyme that breaks down cellulose, especially in the wall structures, and a cellulosome is an array or sequence of enzymes or cellulases which is more effective and faster than a single enzyme or cellulase. In both cases, the enzymes break down the cell wall and/or lipid vesicles and release lipids from the cell. Cellulases used for this purpose may be derived from fungi, bacteria, or yeast. Non-limiting examples of each include cellulase produced by fungus *Trichoderma reesei* and many genetic variations of this fungus, cellulase produced by bacteria genus *Celluiomonas*, and cellulase produced by yeast genus *Trichosporon*. A glycoproteinase provides the same function as a cellulase, but is more effective on the cell walls of microalgae, many of which have a structure more dependent on glycoproteins than cellulose.

In addition, a large number of viruses exist which invade and rupture algae cells, and can thereby release the contents of the cell, in particular stored lipids. Such viruses are an integral part of the algal ecosystem, and many of the viruses are specific to a single type of algae. Specific examples of such viruses include the *chlorella* virus PBCV-1 (Paramecium Bursaria *Chlorella* Virus) which is specific to certain *Chlorella* algae, and cyanophages such as SM-1, P-60, and AS-I specific to the blue-green algae *Synechococcus*. The particular virus selected will depend on the particular species of algae to be used in the growth process. One aspect of the present invention is the use of such a virus to rupture the algae so that lipids inside the algae cell wall can be recovered. In another detailed aspect of the present invention, a mixture of biological agents can be used to rupture the algal cell wall and/or lipid vesicles.

Mechanical crushing, for example, an expeller or press, a chemical solvent recovery step, supercritical fluid extraction, or the like can also be useful in extracting the lipids from lipid vesicles of the algae. Alternatively, mechanical approaches can be used in combination with biological agents in order to improve reaction rates and/or separation of materials.

In some embodiments, algal compounds (e.g. lipids, alkenones, co-products) are extracted from the algal culture 1 (i.e. the dry algal sample prior to extraction) using chemical solvents. Extraction of lipids 7, alkenones 9, and co-products 16 of varying polarities and solubilities can be improved by use of a particular solvent or mixture of solvents. Preferred solvents and solvent mixtures may vary based on the solubility of the desired extracted compound.

The first extraction 2 (i.e. extraction with solvent #1) is performed as a means to isolate the biofuel oil 4 containing the fatty acids, lipids, alkenones, and related compounds of the algal culture 1 from the algal biomass 3. It is important to note that this first extraction with solvent #1 2 is a selective extraction process that enhances the subsequent extractions downstream (i.e. extraction with solvent #2 8, extraction with solvent #3 13). In one embodiment, the algae 1 is extracted with solvent #1 2 to produce a biofuel oil 4 containing alkenones 9 and a biomass 3 containing co-products 16. In another embodiment, the algae 1 is extracted with polar solvent #1 2 to produce a biofuel oil 4 containing alkenones 9 and a biomass 3 containing co-products 16. In an additional embodiment, the algae 1 is extracted in a non-aqueous (i.e. water-free) reaction with polar solvent #1 2 to produce a biofuel oil 4 containing alkenones 9 and a biomass 3 containing co-products 16. In some embodiments, non-polar solvents are generally used (e.g. hydrocarbons 1 to 22 carbons in length, benzene, toluene, cyclohexane, chloroform, ether, 1,4-dioxane, neutral or non-ionic surfactants). In one embodiment, the algal culture 1 is first extracted using n-hexanes. Other embodiments use other hydrocarbons such as pentane, cyclopentane, iso-hexane, n-heptane, iso-heptane, octane, iso-octane, benzene, or toluene. Some embodiments use a combination of non-polar solvents.

Extraction with solvent #1 2 releases many of the algal compounds from the algae culture 1, which can be recovered or separated from the non-aqueous slurry of algae debris material (e.g. cellular residue, enzymes, by-products, etc.) referred to as the algal biomass 3. This can be done by filtration, sedimentation, or centrifugation, with centrifugation often being preferred. In one embodiment, the dehydrated algae culture 1 is mixed with solvent #1 2 and introduced into a Soxhlet or equivalent extraction apparatus to extract the biofuel oil 4 from the algal culture 1.

The recovered biofuel oil 4 comprising fatty acid-rich fractions (e.g. fatty acids, fatty acid derivatives) and lipid-rich fractions can be collected and directed to a specific conversion processes as described in more detail below. Product fractions from the extraction with solvent #1 2 are approximately 60% free fatty acids and 40% lipids, however these ratios may differ up to a 10-20% range. In some embodiments, the lipid content may be 50%, may be 60%, may be 70%, or may be 80% by weight relative to the starting culture 1 using a genetically modified algal source. The algal biomass 3 may also be collected and saved for a separate processing procedure 13 (i.e. extraction with solvent #3) and/or other process as described below for recovery of valuable co-products 16.

Further chemical modifications of the biofuel oil 4, such as esterification, acid-catalyzed esterification, and transesterification, may be employed as a means to produce fatty acid methyl esters (FAMEs) 6, lipids/neutral lipids 7, and/or other by-products such as soap and glycerol. The esterification reaction 5 is conducted using an alcohol, acid or base catalyst, and potentially other reagents like chloroform. In some embodiments, esterification 5 may entail the use of suitable reagents including alcohols comprising a number of carbon atoms ranging from 1 to 20 such as methanol, ethanol, propanol, etc., and an acid or base catalyst(s) such as sulfuric acid, hydrochloric acid, potassium hydroxide, sodium hydroxide, sodium methoxide, or other appropriate reagents. In another embodiment, the reaction is carried out in the presence of a lipase enzyme as a means to enhance the efficiency of the reaction. In other embodiments, the esterification reaction 5 is conducted to allow removal of fatty acids, fatty acid derivatives, and FAMEs 6 to facilitate the purification of lipids 7 and/or the alkenones 9.

Some cases may include spiking the biofuel oil 4 with an internal standard such as ethyl nonadecanoate for quantification of reaction efficiency or chromatography analyses. Other cases involve spiking with purified alkenones 9 with an internal standard.

In many embodiments of the invention, the source alga endogenously produces fatty acids and FAMEs. In some instances then, free fatty acids and/or FAMEs will be present in the biomass 3, and/or biofuel oil-containing fractions 4. In a few preparations, alkenones 9 will be prepared without separating or otherwise removing the endogenous FAMEs, and without the addition of exogenous FAMEs to any fraction(s). In cases where endogenous FAMEs are present in one or more fractions, they will be present at a concentration (wt/v) of less than 80% (4:1) and more preferably less than 50% (1:1) and most preferably less than 20% (1:4), or even less than 15, 10 or 5%. In one embodiment, fatty acids and fatty acid derivatives including FAMEs 6 are separated from the alkenones 9 and discarded. In another embodiment, the neutral lipids 7 are isolated from the FAMEs 6 as a means to produce a lipid-rich fraction substantially free of FAMEs. This lipid-rich fraction may be further modified to produce alkenone derivatives 12 as described below.

Conversions of Algal Lipids to Alkenone Derivatives

In certain embodiments, the subject methods relate to converting algal lipids (e.g. lipids 7, alkenones 9, lipid-rich fraction 7) into alkenone derivatives 12 (i.e. products derived from alkenones or chemical modification of alkenones). By one method, the alkenones 9 are first purified from the other lipids 10 to produce substantially pure alkenones 9 (i.e. a chemical that is chemically pure or analytically pure wherein the chemical has a purity greater than 70%, greater than 75%, greater than 80%, greater than 85%, greater than 90%, greater than 95%, greater than 98%, or greater than 99%.). In some embodiments, the lipid-rich fraction 7 is chemically modified to separate alkenones 9 from other lipids 10 which may be accomplished by several methods such as purification with a solvent or solvents and recrystallization, chromatography, or other suitable process. Another method does not require the alkenones 9 to be first purified from the lipid-rich fraction 7, thus allowing the lipid-rich fraction 7 to be chemically modified to produce alkenone derivatives 12. Additionally, some methods may even be employed to allow a mixture of FAMEs 6, lipids 7, alkenones 9, and other inherent derivatives to be chemically modified to produce alkenone derivatives 12.

Most cases prefer a water-free extraction of alkenones 9 (i.e. no exogenous water added). In some embodiments of lipid/alkenone purification 8, the alkenones 9 are dissolved in a minimal amount of solvent (i.e. low volume), flushed though a filter (e.g. silica gel mesh, column), and purified with the same solvent or one of similar properties wherein the suitable solvent or solvents capable of solubilizing alkenones are primarily polar or have partial polar properties (e.g. chloromethane, dichloromethane, dichloroethane, tetrahydrofuran, dimethylformamide, acetonitrile, nitromethane, propylene carbonate, formic acid, butanol, isopropanol, methyltetrahydrofuran, trifluoromethylbenzene, ethyl acetate, ethyl ether, acetone, dimethyl sulfoxide, alcohols, acetic acid, esters, ethers) now referred to as solvent #2 8. In one embodiment, the polar extraction with solvent #2 8 is performed with dichloromethane, and the purified alkenones are recrystallized with either dichloromethane or n-hexanes. In another embodiment, this reaction 8 proceeds using toluene (PhMe). In one embodiment, the alkenones are extracted using methyltetrahydrofuran. In another embodiment, the alkenones 9 are isolated using acetonitrile. Additionally, dimethyl sulfoxide may be used to extract the alkenones 9.

In another embodiment, the alkenones 9 are purified from other lipids 10 by using a non-polar solvent or solvents (e.g. alkanes, n-hexanes, benzene, toluene, 1,4-dioxane, chloroform, ether). In both cases of polar and non-polar solvent use, the solvent(s) #2 8 may be cooled or evaporated to allow the alkenones 9 to recrystallize to produce a substantially pure alkenone solid material 9. In some embodiments, the alkenones 9 extracted and are then recrystallized using n-hexanes, methyltetrahydrofuran, tetrahydrofuran, dimethyl ether, diethyl ether, methyl-tert-butyl ether, dichloromethane, acetonitrile, dichloromethane, an alkane compound of 1 to 10 carbons, benzene, or other suitable listed solvent or a combination thereof. In certain embodiments, extraction with solvent #2 generally results in an yield of 20%, a yield of 30%, a yield of 40%, a yield of 50%, a yield of 60%, or up to a yield of 80% of purified alkenones 9 (w/w) from the neutral lipids 7 or a total alkenone content at least 3-5% up to 20% (w/w) of the *Isochrysis* dry culture 1. In other embodiments, the substantially pure alkenones 9 are of a purity greater than 50%, greater than 60%, greater than 70%, greater than 80%, greater than 90%, or even greater than 95%.

The purified alkenones 9 may be analyzed by gas chromatography and compared to a set of standards to determine the composition of the alkenones. In some cases, analysis reveals the presence of C37:3, C37:2, C38:2, and C38:3 alkenones along with small amounts of the C39:3 and C39:2 with the most abundant being the methyl 37:3 (where C #:# refers to the number of carbon atoms:number of double bonds). In one embodiment, a complete set of alkenones 9 extracted from the dry culture 1 may range from 35-42 carbons with 2-3 double bonds and methyl or ethyl ketones.

The purified alkenones 9 may be further modified to produce alkenone derivatives 12. Suitable methods allow for the carbon-carbon bonds (e.g. double bonds, single bonds) present in the alkenones 9 to be broken and/or reorganized to produce hydrocarbons (e.g. alkenes, alkanes) and organic hydrocarbon products (e.g. ketones, aldehydes, carboxylic acids, esters, amides, amines, etc.) of a size compatible for biofuel. In some embodiments, the alkenones 9 are converted to biofuel 12 in the hydrocarbon range of 2 to 42 carbons. In some embodiments, the subject methods produce a composition of alkenone derivatives comprising 5 to 20 carbon atoms. In other embodiments, alkenone derivatives are produced comprising 20 to 30 carbon atoms. In other embodiments, the methods produce alkenone derivatives comprising more than 30 carbon atoms. In one embodiment, the subject methods produce a composition of alkenone derivative mixture 12 comprising a C5-C22 hydrocarbon mixture (kerosene/jet fuel boiling range) and under certain conditions, predominantly 8-decen-2-one (C10), 2,9-undecadiene (C12), and 2-heptadecene (C17) as both cis- and trans-isomers.

One process for converting alkenones 9 (purified or mixed with other lipids 10 and/or FAMEs 6) to hydrocarbons is catalytic hydroprocessing, pyrolyzing, or cracking. Catalytic hydroprocessing technology is well known in the art of petroleum refining and generally refers to converting at least large hydrocarbon molecules to smaller hydrocarbon molecules by breaking at least one carbon-carbon bond. However, cracking methods tend to be less selective in location of carbon bond breaking and produce a wider variety of derivatives than other methods such as cross metathesis-type reactions. In some cases, a more diverse mixture of alkenone derivatives 12 is desired; other cases require only specific sized alkenone derivatives 12 to be produced. In cases where hydroprocessing is utilized, the resulting alkenone derivatives are most often a various mixture of smaller hydrocarbon fragments and polymers comprising acrylic acids, acrylic esters, alkenes, vinyl chloride, vinyl acetate, diacids, diamines, diols, plastics, and/or lactic acid. These alkenone derivatives 12 or mixtures of derivatives may not be appropriate for use as a co-produced biofuel source particularly for the use of jet fuel/kerosene biofuel.

In some embodiments, the purified alkenones 9 are converted to alkenone derivatives 12 through a different and separate process than hydroprocessing using a type of cross metathesis reaction 11 (e.g. cross metathesis, olefin metathesis, alkenolysis) in the presence of a catalyst to produce alkenone derivatives 12 with olefin functional groups. Metathesis is a catalytic reaction, generally known in the art that involves the interchange of alkylidene units among compounds containing one or more double bonds (e.g. olefinic compounds) via the formation and cleavage of the carbon-carbon double bonds. Metathesis may occur between two like molecules (often referred to as self-metathesis) and/or it may occur between two different molecules (often referred to as cross metathesis). In the broad sense, the cross metathesis-type reaction 11 involves the rearrangement of carbon double bonds to produce products with olefin functional groups in the presence of a solvent and catalyst. More specifically, cross metathesis reactions occur with more predictable alkene products than hydroprocessing and can produce alkene products derived from alkenones in the necessary size range for uses as jet fuel or kerosene biofuel.

Suitable catalysts include organometallic compounds (e.g. molybdenum-, tungsten-, mercury-, ruthenium-based compounds) or of the like. Suitable solvents comprise alkanes with 1 to 32 carbons (e.g. ethane, butane, pentane, etc.), dichloromethane, dichloroethane, chloroform, benzene, toluene, methyl-tert-butyl ether, and acetic acid and related compounds (e.g. isopropyl acetate, ethyl acetate) although alkenes are preferred solvents in the processing of the alkenones 9. Other present reagents or compounds may include alkenes with 2 to 32 carbons (e.g. ethene, propene, butene, etc.), methyl stearate, ethyl vinyl ether, acrylates, or suitable substitutes.

In one aspect, the cross metathesis-type (i.e. alkenolysis) reaction 11 is butenolysis using a butene reagent. Suitable solvents include chloroform, dichloromethane, chloromethane, and toluene (PhMe) however other solvents capable of efficiently solubilizing the alkenones may be substituted or even added. One butene reagent which may be used is 2-butene which may be in the cis- or trans-chemical orientation, although other embodiments utilize 1-butene, and is preferably added to the reaction in excess. Other reactions such as ethenolysis utilize an ethene reagent (i.e. ethenolysis). In some embodiments, the cross metathesis reaction may be repeated 1 or more times to achieve the most efficient conversion of alkenones 9 to alkenone derivatives 12.

Although this particular type of reaction may be conducted at a range of temperatures from −20° C. up to 100° C., some cases achieve optimum results temperatures ranging from −5° C. to 4° C. or room temperature 20° C. to 30° C. In the case of low temperature reactions, a refrigerated space, ice bath, or other suitable means to chill the reaction may be used. For adequate conversion of alkenones 9 to alkenone derivatives 12, the cross-metathesis-type reaction may require reaction time of 1, 10, 20, 30, or 40 minutes and may take as long as 1 hour, as long as 2 hours, as long as 3 hours, as long as 4 hours, as long as 5 hours, as long as 6 hours, as long as 7 hours, as long as 8 hours, as long as 9 hours, as long as 10 hours, as long as 11 hours, as long as 12 hours, as long as 13 hours, as long as 14 hours, as long as 15 hours, as long as 16 hours, as long as 17 hours, or as long as 18 hours depending on solvents, alkene reagents, alkenone concentration, and catalysts employed. Non-limiting examples are shown in FIG. 15 which provides additional embodiments and associated conditions. In some embodiments, following desired completion of the alkenone conversion, ethyl vinyl ether may be added to quench the reaction.

In certain embodiments, the alkenone derivatives 12 produced by cross metathesis are predominantly 8-decen-2-one, 2-heptadecene, and 2,9-undecadiene. Often, the percentages of 8-decen-2-one, 2-heptadecene, and 2,9-undecadiene present after the reaction are in the range of at least 10%, 20%, and 40%, respectively. In one case, the ratio of cross metathesis products 8-decen-2-one, 2-heptadecene, and 2,9-undecadiene by gas chromatography analysis is typically 1:2:2.5, respectively. Products 8-decen-2-one and 2,9-undecadiene are often present in a trans:cis chemical orientation of 3:1 to 4:1, respectively. Other alkenone derivatives may comprise 15-heptadecen-2-one, 9-undecen-3-one, 16-octadecen-3-one, and 2-nonadecene along with trace other products.

The long chains of carbon in the alkenones 9 produced by algae (e.g. 30 to 42 carbons) can be used to produce a wider range of biofuels or lubricating oils than those derived from glycerides (e.g. 5 to 22 carbons). In another embodiment, unpurified alkenones comprising a mixture of alkenones 9, lipids 10, FAMEs 6, etc. are converted to hydrocarbons without separating the FAMEs 6 from the lipids 7 prior to hydroprocessing or cross metathesis-type reactions 11. Furthermore, another embodiment allows the unpurified alkenones comprising only the lipid-rich fraction 7 to undergo cross metathesis 11 to produce alkenone derivatives 12.

In certain embodiments, the subject methods comprise converting algal alkenones 9 into a liquid fuel such as diesel or gasoline. In other embodiments, the subject methods comprise converting algal alkenones 9 into a gaseous fuel, such as a syngas (a mixture of CO and $H_2$) and/or a synthetic hydrocarbon gas (e.g. methane, propane, and butane).

In certain embodiments, the subject methods comprise converting the long chains of the alkenones 9 into methane and supercritical carbon dioxide by technologies that use high temperature liquid metal chemistry. Such technologies are known in the art. For example, algal biomass 3 may be converted into methane via hydrothermal processes. Optionally, growing of algae and hydrothermal processing of algae culture 1 may be coupled into a continuous process. It may be possible to introduce the algal culture 1 directly into a reactor for hydrothermal gasification. Thus, this approach may allow the use of the algae cells 1, directly without first extracting the algae biofuel oil 4, for the production of hydrocarbons or polymers, eliminating several costly steps such as solvent extraction.

Analysis and quantification of the resulting alkenone derivative composition 12 and reaction efficiency may utilize $^1$H nuclear magnetic resonance ($^1$H NMR) spectroscopy using a solvent such as CDCl3 or of the like. One-dimensional gas chromatography with flame ionization detection (GF-FID), two-dimensional gas chromatography with flame ionization detection (GC×GC-FID), time of flight mass spectrometry (GC×GC-TOF), and gas chromatography-mass spectrometry (GC-MS) may also be applied for further reaction analysis.

Recovery of Commercially Valuable Co-Products

In addition to the production of biodiesel 6, biofuel 12, and other alkenone derivatives 12, a parallel (i.e. simultaneous, coordinated) extraction method may be employed to isolate other commercially valuable co-products (e.g. products derived from the algae biomass 3, products produced by chemical modification of the biomass 3, of which have monetary value) from the algal culture 1, more specifically the algal biomass 3 (i.e. the residual algal debris material of the initial extraction 2). In particular, this complementary method utilizes the waste-stream normally discarded in the production of biodiesel 6 to produce valuable co-products 16 without the disruption or alteration of the algae-to-biodiesel/algae-to-alkenone derivatives processes. Upon preparing the algae culture 1 for the extraction with solvent #1 2 to extract the biofuel oil 4, the algal biomass 3 may be separated and further processed through an additional method described below.

In one embodiment, the biofuel oil 4 is extracted from a non-aqueous algal culture slurry 2 in the presence of a non-polar solvent #1. Solvent #1 2 may then be evaporated, and the biofuel oil 4 may be isolated using a filter, membrane, separatory funnel, extraction thimble, or similar means to remove the biofuel oil 4 from the algal biomass 3. In some cases, an extraction apparatus such as a Soxhlet extractor may be used; other cases do not require the use of a Soxhlet extractor or comparable apparatus. As mentioned above, the initial non-polar extraction with solvent #1 2 selectively solubilizes and removes alkenones 9 from the algal biomass 3 which results in an enriched and more purified co-product-containing biomass 3 substantially free of alkenones 9 (i.e. at least 70%, 80%, 90%, or greater than 95% free of alkenones). A polar extraction 13 with a solvent such as ethanol without a prior non-polar extraction 2 would non-selectively pull down a wider range of compounds (i.e. contaminants) and would require additional selective partitioning with water to achieve the same results.

The algal biomass 3 (i.e. the biomass fraction) removed of the biofuel oil 4 can be combined with one or more suitable solvents 13, now referred to as solvent #3, to further extract the biomass oil 14 (i.e. biomass oil fraction) containing the algal co-products 16. Such suitable solvents may comprise polar solvents (e.g. chloromethane, dichloromethane, dichloroethane, tetrahydrofuran, methyltetrahydrofuran, ethyl acetate, acetone, dimethyl sulfoxide, alcohols, acetic acid, esters, ketones, amines, carboxylates, halogenated hydrocarbons), non-polar solvents (e.g. hydrocarbons 1 to 22 carbons in length, benzene, toluene, chloroform, dimethyl ether, n-hexanes, iso-hexanes), and surfactants although this extraction 13 is most often performed with a polar solvent. In one embodiment, a polar solvent 13, more specifically an alcohol such as ethanol, is added to the algal biomass 3 to release the biomass oil 14. In another embodiment, the polar solvent methanol is used to extract the biomass 3.

In embodiments of the extraction with solvent #3 13, the extraction is conducted in the dark or a minimal amount of light (e.g. dim light, no light) to prevent decomposition or photo-oxidation. In some embodiments, the term "minimal amount of light" is 0 seconds, less than 5 seconds, less than 10 seconds, less than 15 seconds, less than 30 seconds, less than 1 minute, less than 2 minutes, less than 5 minutes, and up to less than 10 minutes. In another embodiment, the extraction may be carried out in a certain spectrum of light such as red light or other specific light range as to limit photo-oxidation. Other algal biomass extractions 13 may not require dark conditions depending on the desired co-products 16 to be isolated.

In order to effectively extract co-products 16, a proper ratio of solvent(s) 13 to algal biomass 3 (w/v) may be considered. In some cases, a ratio greater than 20:1 solvent/algal biomass is sufficient while other cases may require higher concentrations of solvent more on the order of greater than 30:1 or even 40:1. Other extractions may only effectively work under a lower solvent/algal biomass ratio less than 20:1, 10:1, 5:1, ranging down to 1:1.

Temperature and time are also of concern in the extraction of co-products 16. While some co-product extractions 13 benefit from proceeding below 45° C., 25° C., 10° C., 4° C. or even 0° C., other extractions may be performed at higher temperatures greater than 25° C., 30° C., 40° C., or 45° C. Under certain parameters, extraction at 45° C. may not be suitable to prevent decomposition of the desired extracted co-products 16. Extraction time can also affect the resulting co-product yields 16, of which can vary from as little as 1 minute to more than 240 minutes and possibly spanning overnight or over several days. In some embodiments, optimum yields are acquired only after extraction for a time period longer than 2 hours. In another embodiment, the biomass 3 is extracted for at least 10 minutes.

The subsequent biomass slurry with solvent #3 13 may be dried by evaporation using a rotary evaporator or other means (e.g. vacuum drying, drum drying, hot air exposure (e.g. convective or direct drying), dielectric drying, supercritical drying, natural air drying, etc.) and subjected to filtering or like means to separate the fluid phase from the residual solid biomass material resulting in the isolated biomass oil 14.

In some cases, the biomass oil 14 may be further modified or fractionated to produce additional co-products 16. In one embodiment, the biomass oil 14 is fractionated by chromatography 15 (e.g. flash chromatography, high-performance liquid chromatography, liquid chromatography). Chemical standards such as a fucoxanthin standard may be spiked into the biomass oil 14 as an internal reference for comparison. The resulting fractions may be analyzed by $^1$H NMR spectroscopy using a suitable solvent. Absorbance spectroscopy, high performance liquid chromatography, or gas chromatography may be applied for additional analysis.

Suitable chromatography 15 solvents may include one or more n-hexanes, ethyl acetate, ether, acetone, toluene, petroleum ether, dichloromethane, methanol, hydrocarbons or of the like as well as specific ratios of solvents to obtain optimum purified fraction products. In one embodiment, a mixture of n-hexanes and ethyl acetate is used in a ratio ranging from 1:1 to 10:1, respectively. Other embodiments do not use an n-hexanes/acetone mixture or at least not in a ratio 6:4, respectively.

One commercially valuable fraction that may be obtained through this method contains a carotenoid or carotenoids, particularly fucoxanthin 16 (e.g. trans-fucoxanthin, cis-fucoxanthin, fucoxanthin-related compounds) which may be subjected to further purification if necessary. In one embodiment, at least 50% up to 80% or even 90% of the total extracted fucoxanthin 16 is contained and obtained from the biomass oil 14.

In one embodiment wherein the 30 g of dry algal culture 1 is extracted with n-hexanes as solvent #1 2, yields of biofuel oil 4 may be near 4-7 g and further extraction of the biomass 3 with ethanol as solvent #3 may isolate 2-5 g of biomass oil 14 from the biomass 3, producing yields of 0.01 to 0.6 g of fucoxanthin 16. Furthermore, a 30 g dry culture 1 extracted by solvent #2 2 and solvent #3 13 may yield an average total fucoxanthin extract 16 from *Isochrysis* dry samples at least 5 mg/g, 10 mg/g, 20 mg/g, 30 mg/g dry weight or 0.5%, 1%, 2%, 3% (w/w), respectively. Depending on the batch of starting culture, fucoxanthin yield may average 0.5%, 1%, and possibly up to 3%, 4%, or more than 5% (w/w) of the starting culture.

In another embodiment, a dry algae culture 1 of 50 g is extracted to produce about 10 g of biofuel oil 4 and about 2 g of biomass oil 3 (5:1 ratio, respectively). The biofuel oil 4 is further modified to produce approximately 5.4 g of FAMEs 6 and 1.6 g of alkenones 9 (27:8 ratio, respectively). Modifying the biomass oil yields near 0.4 g of fucoxanthin 16. In a parallel co-production of FAMEs 6, alkenones 9, and fucoxanthin 16, the extraction of a single batch of algae produces a ratio of 27:8:1, respectively. In other embodiments, the yield of FAMEs 6 may be closer to 2 g, 4 g, 8 g, or 9 g (ratio of 10:8, 20:8, 40:8, or 45:8 FAMEs:alkenones). In some embodiments, yields of alkenones 9 are 0.5 g, 1 g, 2 g, 4 g, and up to 6 g (ratio of 27:2.5, 27:5, 27:10, 27:20, and 27:30 FAMEs:alkenones). In other embodiments, co-product or more specifically fucoxanthin 16 extraction yields are near 0.01 g, 0.1 g, 0.2 g, 0.4 g, 1 g, or 1.5 g (ratio of 0.2:32, 2:32, 4:32, 8:32, 20:32, or 30:32 co-product:alkenones).

In some cases, it may be greatly important to produce both the cis and trans isomers of fucoxanthin. Algae species of the *Isochrysis* family produce both isomers as compared to some algae which only produce one isomer or very limited amounts of one isomer. Other cases may benefit from only producing the cis or the trans isomer of fucoxanthin depending on the desired future use of the isolated compound.

Example 1

The following example describes a specific embodiment of the inventive method to produce alkenones and alkenone derivatives, which is included to further illustrate certain aspects of the invention and are not intended to limit the invention.

Introduction

In preparation for a future 1-acre-sized bio-production site in Cape Cod, Mass., USA (41° 33 05"N, −70° 36 55"W), we surveyed local species capable of sustainable growth and high production of FAMES in the low incidence of annual light availability and cool temperatures of the region. One of our targeted algae was the coastal marine prymnesiophyte *Isochrysis* sp. including strains T-Iso and C-Iso. We were interested in *Isochrysis* sp. as they are rich in polyunsaturated fatty acids (PUFAs), can be grown both indoors and outdoors (D. Kaplan et al., CRC Press, F L, 1986, pp. 147-198), have no cell walls, and are grown commercially for mariculture feedstocks (P. Lavens and P. Sorgeloos, Manual on the production and use of live food for aquaculture, Fisheries Technical Paper 361, Food and Agriculture Organization of the United Nations, 1996; M. Albentosa, et al. Aquaculture, 1996, 148, 11-23; C. T. Enright, et al., Journal of Experimental Marine Biology and Ecology, 1986, 96, 1-13). Furthermore, this effort conforms to the future fuels strategy proposed by Inderwaldi and King stressing the importance of in-depth scientific analysis of short, medium, and long-term aspects of biofuel production (0. R. Inderwildi and D. A. King, Energy & Environmental Science, 200, 2, 343-346).

Methods and Materials

1. Microalgal Species and Culture Conditions.

Two *Isochrysis* sp. strains "T-Iso" and "C-Iso" and the diatom, *Thalassiosira weissflogii* strain "TW" were sourced from the Milford Laboratory Microalgal Culture Collection (Milford, Conn.). Additional information on the "T-Iso" and "C-Iso" strains have been described in detail (G. H. Wikfors and G. W. Patterson, Aquaculture, 1994, 123, 127-135). In this study, we included TW to highlight differences in lipid profiles of algae. Microalgae were cultured in 250 ml glass Erlenmeyer flasks under 24 hour lighting (approximately 31 μmol. photons m-2 s-1) and held on an oscillating shaker (100 rpm) at 19° C. Standard F/2 media was used for cultures with silica provided for the comparison "TW" strain. Microalgae were harvested by centrifuging at 4,000 rpm and decanting the supernatant. The remaining algal pellet was freeze-dried.

2. Extraction of Algal Samples.

Freeze-dried algal biomass (10 to 50 g) were extracted with hexane. The resultant lipid extract was spiked with an internal standard, ethyl nonadecanoate, and transesterified under N2 using 10% methanolic HCl in hexane (55° C.; 12 hours). We used ethyl nonadecanoate to check both the completeness of the transesterification reaction by monitoring the production of methyl nonadecanoate and using the latter for quantification purposes. The reaction products were extracted with hexane, reduced in volume, spiked with an external standard, n-heptadecane, and stored until analysis by the GC-FID.

3. Analysis by Gas Chromatography with Flame Ionization Detection (GC-FID).

We quantified FAMEs and alkenones in the esterified samples using a Hewlett-Packard 5890 GC-FID. Compounds were separated on a glass capillary column (J&W DB-1MS, 30 m, 0.25 mm i.d., 0.25 μm film thickness) with H2 carrier gas. FAMEs were identified with standards purchased from Nu-Chek Prep (Elysian, Minn.) and Supelco (Bellefonte, Pa.). Alkenones were identified based on comparison to published elution order on gas chromatographic columns, their mass spectra, and mixtures harvested from cultures of *Isochrysis* sp. Methyl nonadecanoate recoveries were always >90%. No ethyl nonadecanoate was observed in the samples.

Example 2

The following example describes a specific embodiment of the inventive method to simultaneously produce alkenones and alkenone derivatives in parallel with the production of fucoxanthin, which is included to further illustrate certain aspects of the invention and are not intended to limit the invention.

Introduction

The need for new energy supplies to meet a growing global demand and a desire for renewable, sustainable, and domestic feedstocks continues to drive much research aimed at investigating alternative energy sources. Recently, there has been a great resurgence of interest in algae as a potential biofuel feedstock; particularly for the production of liquid fuels such as biodiesel and other biomass-derived oils. Proposed benefits include the avoidance of certain fuel vs. food controversies and reportedly higher productivities when compared to traditional agricultural crops. Criticisms of algal biofuel programs tend to focus on projected costs of the overall process, essentially echoing one conclusion from Sheehan's report on the United States Department of Energy-sponsored Aquatic Species Program (ASP). The ASP was started in 1978 for the purpose of investigating transportation fuel from algae and was defunded in 1996 primarily because projected costs were in the range of $40-60 per barrel (42 gallons=159 L) compared to $18.46 for crude petroleum at that time. While the cost of petroleum has increased dramatically in recent years, critics remain who contend that nonetheless algal biofuels will prove too costly. For instance, in a recent perspective on microalgal transportation fuels, van Beilen argues that algae productivities do not surpass those of irrigated tropical crops and cultivating, harvesting and processing microalgae is simply too expensive. The author goes on to state that "only if the algal biomass is a byproduct of . . . the production of high-value compounds such as astaxanthin or beta-carotene, commercially viable energy production from algal biomass might be feasible." Many others including Chisti and Wijffels have stressed the importance of value added co-products as a necessary component of algal biofuel production. The United States Department of Energy (DOE) "National Algal Biofuels Technology Roadmap" goes on to identify valuable co-products as one of the key reasons for exploring algae as a source of biofuels.

Figure 2:
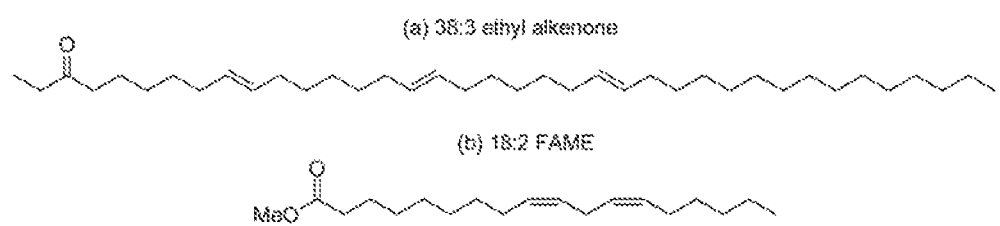
FIG. 2 shows structures of a common alkenone 9 produced by *Isochrysis* sp. (a) and common FAME methyl linoleate 6 (b). Nomenclature for both is # of carbons:# of double bonds, however, note that the configuration of double bonds is different.

Recently we have focused on *Isochrysis* as they produce a unique and promising class of lipids known as long-chain alkenones. These compounds are unlike the cis-unsaturated methylene interrupted fatty acid components of triacylglycerols (TAGs) as they typically have two to four trans-alkenes occurring at 7-carbon intervals (FIG. 2). At colder growth temperatures, alkenones are more highly polyunsaturated, and the proportion of diunsaturated isomers of the C37 methyl alkenone (the so-called "unsaturation index") has been widely adopted by geochemists as a proxy for past sea surface temperatures. *Isochrysis*, is one of several species of haptophyte marine microalgae including the widely distributed coccolithophore *Emiliania huxleyi* and the closely related species *Gephyrocapsa oceanica* that biosynthesize alkenones and the related alkenoates and alkenes, known collectively as PULCA.

Alkenones are thought to reside in cytoplasmic lipid bodies and can be more abundant than TAGs especially in the stationary growth phase. Under nitrogen or phosphorus limitation, up to 10-20% of cell carbon in the stationary phase is accumulated as predominantly triunsaturated alkenones. Evolutionarily, alkenones may have been favored over TAGs because their trans-double bond geometry provides a more photostable form of energy storage. This unusual geometry has also been suggested to contribute to their limited degradation by grazers in surface waters of the ocean.

Haptophytes had been included in several reviews and other reports related to biofuels, but until recently alkenones were not discussed in any of these studies. In one study of 55 microalgal species for biodiesel production, *Isochrysis galbana* proved to be average in both biomass yield and lipid productivity. Average lipid content in 15 nutrient-replete and nitrogen-deficient cultures was 25% and 29% dry weight, respectively.

We were attracted to haptophytes in part because *Isochrysis* is one of only a select number of algal species farmed industrially, harvested for purposes of mariculture, and therefore is representative of the scale necessary for biofuel production. In an effort to produce biodiesel (FAME) from *Isochrysis*, we recently described results from the acid-catalyzed esterification of the total hexanes extract ("biofuel oil"). This material contained a significant amount of alkenones (14% w/w), and contamination by these high-melting (~70° C.) components is detrimental to cold flow fuel properties. More recently, a method for producing an alkenone-free *Isochrysis* biodiesel was reported using a saponification/separation procedure. While this sequence adds additional steps to the overall process, in addition to supplying a superior quality biodiesel, it also generates an alkenone-rich neutral lipid fraction as a potential secondary product stream.

We argue that alkenones represent a potentially fruitful and as yet unexplored renewable carbon source with structures particularly well suited for a number of catalytic processes. Specifically, alkenones feature long olefinic carbon-chains, favorable carbon-to-hydrogen ratios, and few heteroatoms (i.e. no sulfur or nitrogen and C:O~37-40:1, ref. FIG. 2). Key differences relative to fatty acids include a much longer hydrocarbon backbone, more widely spaced trans-double bonds, and a ketone functional group (FIG. 14). Alkenones are also fundamentally different than the terpenoid botryococcenes that have received significant attention as a potential algal biofuel source, despite the noted slow growth habit of *B. braunii* which poses concerns about its suitability as a biofuel feedstock. PULCAs thus represent an unexplored source of renewable carbon biosynthesized by robust algal species that could provide access to a unique suite of products unobtainable from other oil feedstocks.

Herein we report a method a series of selective extraction techniques for the parallel production of biodiesel and isolation of several valuable co-products including an alkenone hydrocarbon mixture of the kerosene/jet fuel range (primarily C10-, C12-, and C17-hydrocarbons) and fucoxanthin, a high-valued carotenoid, from marine microalgae. *Isochrysis* is produced industrially for purposes of mariculture and has been included in several reviews and numerous reports related to biofuels. Aside from its availability on large-scale, other attractive attributes of *Isochrysis* as a biofuel feedstock include favorable growth characteristics and high lipid content. While there has been much discussion about the potential for the isolation/production of value added co-products to augment algal biofuel production (the so-called "biorefinery" concept), to the best of our knowledge this is the first report with experimental data from a successful method for combined biodiesel production and valuable co-product isolation from an algae feedstock.

Materials and Methods

1. Microalgal Species and Culture Conditions.

The marine microalgae *Isochrysis* sp. "T-iso" used in the present study although *Isochrysis* sp. "C-iso" is also suitable. The marine microalgae *Isochrysis* sp. "T-iso" was purchased from Reed Mariculture (strain CCMP1324) (Santa Cruz, Calif.) who has grown this species for nearly 20 years as a primary feed in shellfish and shrimp hatcheries. The algae were grown in greenhouse ponds under natural sunlight in a modified F/2 media. Average water temperatures were 18 to 20 C. Approximately 1 kilogram of wet biomass (20% biomass w/w) was harvested by centrifugation and decanting of the supernatant and then lyophilized in ~30 g batches which gave ~150 g of dry *Isochrysis* sp. biomass as a greenish, dark-brown solid.

2. Extraction of the Biofuel Oil from the Algal Biomass.

The dry *Isochrysis* culture was extracted in 30 to 50 gram batches with n-hexanes in a Soxhlet extraction apparatus. The Soxhlet apparatus was allowed to cycle for 24-48 hours (until the color of the solvent was a faint yellow). Hexanes were removed with a rotary evaporator, and the weight of the n-hexanes-extractable material (now referred to as the biofuel oil) was recorded. The residual biomass was retained from the extraction thimble for further use.

3. Isolation of Fatty Acids and Lipids from the Biofuel Oil.

After extraction from the biomass, the biofuel oil was processed in a transesterfication reaction by treating the biofuel oil with KOH at 60° C. for 3 hours. The resulting saponified acylglycerols were selectively partitioned into water while the neutral lipids extracted with n-hexanes. Reacidification of the aqueous phase with HCl and extraction with n-hexanes produced the free fatty acids (FFAs). The overall mass recovery for combined FFAs and neutral lipids from the algal oil is typically quantitative (40% neutral lipids+60% FFAs).

4. Isolation and Purification of Alkenones from the Neutral Lipids.

Neutral lipids (10 g) were dissolved in a minimal amount of dichloromethane and flushed through silica gel (230-400 mesh, 100 g) with pressure using dichloromethane (approximately 150 mL) as eluent. The solvent was then removed on a rotary evaporator, and the resulting orange-colored solid was recrystallized in n-hexanes to give pure alkenones (typically 4 g) as a white solid.

5. Alkenone Cross Metathesis and Analysis of Co-Product-salkenone Derivatives.

The purified alkenones were further chemically modified by cross metathesis reaction wherein 2-butene (i.e. butenolysis) was used although other substitutions are possible as well. 2-Butene (0.2 mL, 15 equiv.) was condensed in a reaction flask at −78° C. under a nitrogen atmosphere. Alkenones (100 mg), methyl stearate (methyl octadecanoate) (56 mg), dichloromethane or toluene (1.0 mL), and catalyst (2 mol %, 2-3 mg) were then added and the resulting heterogeneous mixture was placed in a refrigerator (4° C.) or ice bath (0° C.) for the allotted time. Reactions conducted were quenched with ethyl vinyl ether (0.9 mL, 50 equiv.) and stirred for 15 minutes before concentrating on a rotary evaporator and analyzing by $^1$H NMR and gas chromatography.

6. Analysis of Alkenones and Alkenone Derivatives.

Analysis by $^1$H nuclear magnetic resonance ($^1$H NMR) spectroscopy. $^1$H NMR spectra of the purified alkenones and cross metathesis reaction mixtures were obtained under ambient conditions using CDCl3 as solvent, which also served as internal reference (shift value of residual proton at 7.26 ppm).

Analysis by one-dimensional gas chromatography with flame ionization detection (GC-FID) and gas chromatography-mass spectrometry (GC-MS). The purified alkenones and butenolysis reactions were analyzed on a Hewlett-Packard 5890 Series II GC-FID. Samples (1 μl) were injected cool-on-column and separated on a 100% dimethyl polysiloxane capillary column (Restek Rtx-IMS, 30 m length, 0.25 mm I.D., 0.25 μm film thickness) with H2 as the carrier gas at a constant flow of 5 mL min-1. The GC oven was programmed from 70° C. (7 min hold) and ramped at 6° C. min-1 to 320° C. (15 min hold). Percent conversions for the butenolysis reactions were determined by comparison of integration ratios for combined alkenones (rt=44-48 min) to methyl stearate (retention time=27.5 min) relative to a starting alkenone/methyl stearate standard mixture. Select samples were also analyzed by GC-MS on an Agilent 6890 GC with a 5973 MSD. Splitless 1 μL sample injections, were separated on a DB-XLB capillary column (60 m×0.25 mm×0.25 μm film thickness) using helium as the carrier gas (10.5 psi constant pressure), and the following GC temperature program: 4 min at 40° C. and ramped to 320 at 5° C./min (held 15 min).

Analysis by comprehensive two-dimensional gas chromatography with flame ionization detection (GC×GC-FID) and time of flight mass spectrometer (GC×GC-TOF). Select cross metathesis reaction mixtures were analyzed by GC×GC-FID and GC×GC-TOF MS according to previous described methodologies.

7. Ethanol Extraction of the *Isochrysis* Biomass.

After the Soxhlet extraction with n-hexanes, the residual biomass was submerged in ethanol (200 ml) for an allotted time. Care was taken at this stage to ensure that the samples and subsequent materials were exposed minimally to light. The biomass was then removed by filtration into a tared round bottom flask and the ethanol removed with a rotary evaporator. Weights of the ethanol-extracted materials were recorded now referred to as the biomass oil.

8. Analysis and Isolation of Biomass Oil-Derived Co-Products.

Analysis by $^1$H nuclear magnetic resonance ($^1$H NMR) spectroscopy. $^1$H NMR spectra of the biomass oil, a fucoxanthin-enriched biomass oil, and a fucoxanthin standard were obtained on a Varian Inova 500 MHz spectrometer under ambient conditions using CDCl3 as solvent, which also served as internal reference (shift value of residual proton at 7.26 ppm). The fucoxanthin-enriched biomass oil was obtained by flash chromatography of biomass oil on silica using an automated Combiflash Rf system (Teledyne Isco): 1.9 g biomass oil, 24 g silica cartridge, 15 minute run time, gradient from 100% hexanes to 100% ethyl acetate. Fractions that were bright red in color and mostly pure by TLC (1:1 hexanes ethyl acetate, Rf fucoxanthin=0.36) were combined into a tared round bottom flask and concentrated on a rotary evaporator in the dark. The weight of the fucoxanthin-enriched biomass oil was recorded, and the fucoxanthin content analyzed by $^1$H NMR and HPLC (vide infra).

Absorbance spectroscopy. Fractions obtained by chromatography of the neutral lipids on silica were red in color, and their pigment content was examined by absorbance spectroscopy. These fractions were concentrated in vacuo and redissolved in n-hexanes to a concentration of 50 mg/mL. A fucoxanthin standard was purchased (Sigma-Aldrich), and a sample prepared as above for comparison. Absorbance between 300 and 800 nm was measured using a Jasco V-670 spectrophotometer.

Analysis and quantification of fucoxanthin by HPLC. Fucoxanthin contents in the biomass oil were quantified using a Varian ProStar HPLC system. The system consisted of a binary pump, 410 auto-sampler, and Photodiode Array Detector. Separation was carried out with a C18 column (Waters length 250 mm×i.d 4.6 mm×particle size 5 μm). The mobile phase (100% methanol) was eluted at a flow rate of 1 mL/min. Detection wavelength was set at 446 nm. Quantification of fucoxanthin was carried out by means of a calibration curve, constructed by analyzing fucoxanthin samples (purchased from Sigma-Aldrich) at concentrations of 0.016-1.0 mg/mL with R2=0.9987.

Results and Discussion

Hexanes extraction for biodiesel production. Previously, we have reported on the production of a biodiesel from *Isochrysis* using standard methods involving extraction of dry algal culture with n-hexanes. After removal of the n-hexanes in vacuo, the resulting green/black grease-like biofuel oil can be converted to a crude biodiesel by acid-catalyzed esterification. Biodiesel produced by this method is approximately 40% non-fatty acid methyl ester (non-FAME, i.e. non-biodiesel) components that include a unique class of lipids biosynthesized by *Isochrysis* known as poly-unsaturated long-chain alkenones. The significant amount (14% w/w) of these high-melting alkenones leads to severe cold-flow fuel property issues.

An alkenone-free *Isochrysis* biodiesel can be achieved by treatment of the biofuel oil with potassium hydroxide resulting in saponification of the triglycerides and formation of the corresponding water-soluble carboxylate salts (soaps). Alkenones along with other neutral lipids are then selectively partitioned into a hexanes layer before the aqueous soaps are re-acidified and converted to biodiesel. This purified biodiesel has markedly improved cold-flow with no trace of alkenone contamination and is now 95% FAME. The mass balance for the saponification process is quantitative (60% FFAs+40% neutral lipids) and does not affect the FAME profile of the resulting biodiesel.

While saponification introduces additional steps into the biodiesel synthesis, not only is the biodiesel obtained of higher quality, it also allows for the recovery of a neutral lipid fraction from the original biofuel oil as a potential secondary product stream in line with recommendations from the U. S DOE "National Algal Biofuels Technology Roadmap". Our primary interest in this regard has been with the alkenones which comprise approximately 40% (w/w) of the neutral lipids obtained by saponification and separation of the biofuel oil.

Isolation and Purification of Alkenones as a Byproduct of Biodiesel Production.

Figure 3:
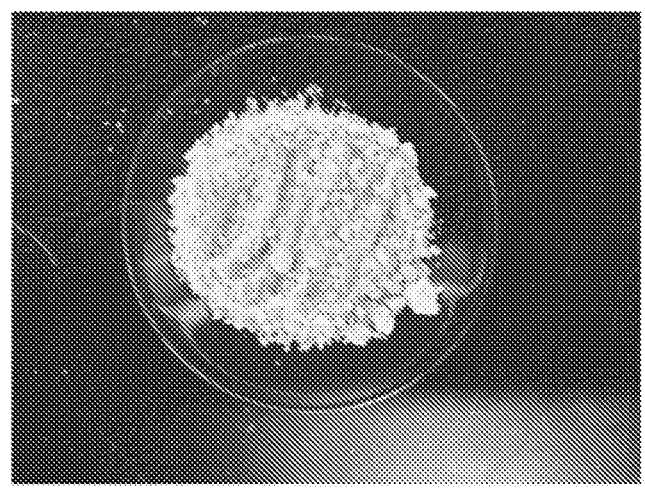
FIG. 3 shows pure alkenones 9 showing that these compounds are white, crystalline solids at room temperatures isolated in multi-gram quantities from *Isochrysis* (typically 4 g from 25 g of the biofuel oil 4).

Prior to attempting any reactions, we isolated and purified the alkenones from the neutral lipid fraction containing other compounds including pigments such as chlorophylls and carotenes. This was challenging due to the low solubility of alkenones in a variety of organic solvents (e.g. n-hexanes, diethyl ether, acetone, ethyl acetate). After some optimization, the dark-colored pigment-containing material could be removed by flushing the material through silica using a minimal amount of dichloromethane (DCM) as eluent. Upon removal of the solvent, the resulting orange-colored solid was further purified by recrystallization with n-hexanes affording analytically pure alkenones as a white solid (FIG. 3). This procedure generally resulted in 40% isolated yield (w/w) from the neutral lipids or 3.2% of the *Isochrysis* dry culture, which is close to the total alkenone content of 5% that we determined previously. Analysis of the purified alkenones by gas chromatography and comparison to standards revealed the presence of C37:3, C37:2, C38:2, and C38:3 alkenones along with small amounts of the C39:3 and C39:2 with the most abundant being the methyl 37:3 (where C #:#refers to the number of carbon atoms:number of double bonds, see FIG. 2).

Cross metathesis of alkenones with 2-butene. Results from the cross-metathesis reactions of isolated alkenones with 2-butene using Grubbs' first- (Ru—I) and second-generation (Ru-II) catalysts, and Ru-HG are summarized in FIG. 15.

Figure 11:
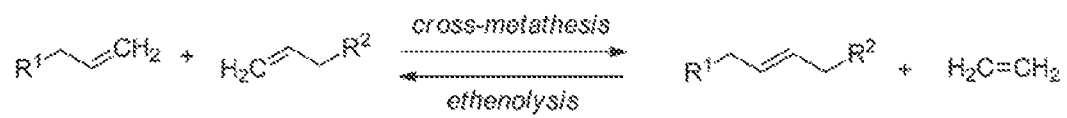
FIG. 11 shows cross metathesis (CM) and the reverse ethenolysis 11.

Olefin metathesis has long been embraced by the synthetic organic and polymer communities, often used to create larger molecules from small alkene-containing starting materials as in the case of cross metathesis (FIG. 11). These reactions typically occur with the extrusion of ethylene gas, which serves as an entropic driving force. The opposite process, i.e. addition of ethylene across a double bond ("ethenolysis"), would thus create two smaller sub-units. Ethenolysis of FAMEs and other fatty acid derivatives using Grubbs'-type ruthenium initiators has been abundantly reported as a method for producing valuable smaller hydrocarbon mixtures from renewable feedstocks.

Figure 12:
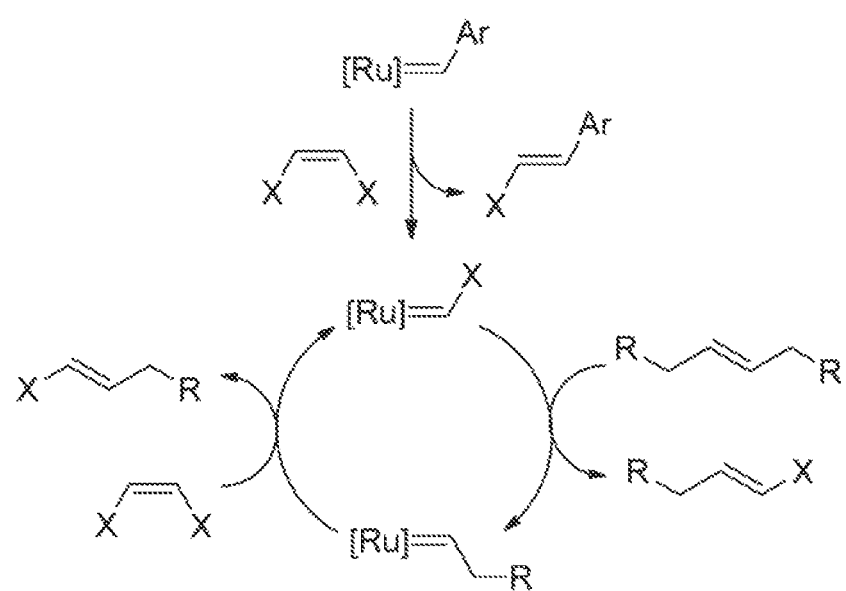
FIG. 12 shows a mechanism of ethenolysis (X=H) and butenolysis (X=CH3) 11.

One challenge associated with ruthenium-catalyzed ethenolysis is that the reaction requires propagation of a ruthenium methylidene species that is prone to decomposition (X=H, FIG. 12). Additionally, the terminal olefin products can undergo the reverse self-metathesis and so yields tend to be modest (~40-60%). One strategy to improve this approach is to use 2-butene in place of ethylene (X=Me), thus avoiding formation of a ruthenium methylidene and producing methyl-capped alkene products that are less reactive toward self-metathesis.

Figure 13:
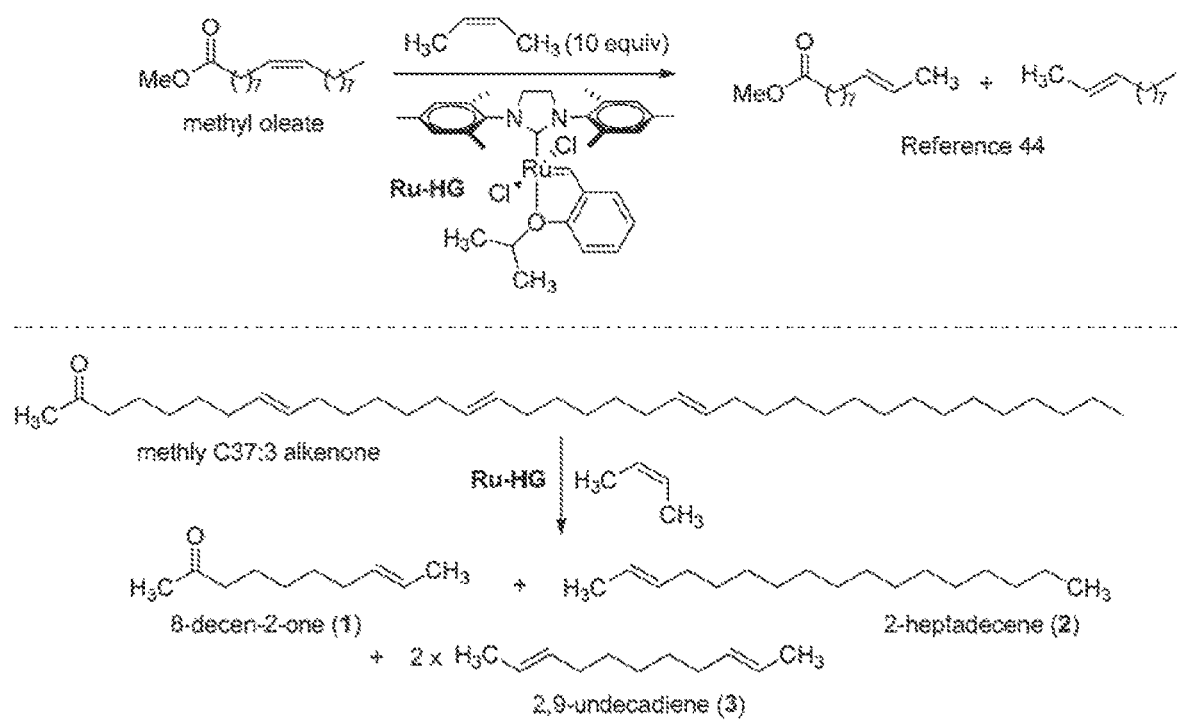
FIG. 13 shows comparison of methyl oleate and alkenone butenolysis reactions 11.

Patel and coworkers reported the rapid and high-yielding cross-metathesis reaction of methyl oleate (Methyl (9Z)-octadecenoate) with 2-butene using the second-generation Hoveyda-Grubbs catalyst (Ru-HG) to produce methyl 9-undecenoate and 2-undecene (FIG. 13). Applied to long-chain alkenones, certain fundamental differences between the alkenones and FAMEs made success of this reaction uncertain (ref. FIG. 2 and FIG. 14). First, again the alkenones contain trans-alkenes as opposed to the more metathesis-reactive cis-configured double bonds found in FAMEs. Second, alkenones have limited solubility in the organic solvents used to perform olefin metathesis, particularly at the cold temperatures required to condense 2-butene (trans-2-butene bp=0° C.). It was therefore unclear whether the alkenones would even dissolve and if so whether the catalyst would engage the alkenone trans-double bonds at these low temperatures.

All butenolysis reactions were performed using an excess of 2-butene (15 equiv., calculated as 5 equiv. per alkene for the most abundant (37:3) alkenone in the starting mixture) to drive the equilibrium toward products and 2 mol % (calculated as above) of the catalyst. After 18 h at 4° C., the alkenones were consumed when using catalysts Ru-II and Ru-HG (entries 1-3), whereas Ru—I gave only 70% conversion under these same conditions (entry 4). Patel and coworkers reported very low conversions (<1%) for the butenolysis of methyl oleate with cis-2-butene (10 equivalents) using both Ru—I and Ru-II, however those reactions were conducted at lower temperature (−5° C.), catalyst loading (0.1 ppt), and times (2 h). Near quantitative conversion of methyl oleate was reported by Patel et. al when using Ru-HG at −5° C. for two hours and upon closer examination was essentially complete within 30 minutes. Butenolysis of alkenones using either cis- or trans-2-butene with Ru-HG appeared similarly rapid with 100% conversion observed after 1 h (Entries 6 and 7, FIG. 14).

Figure 4:
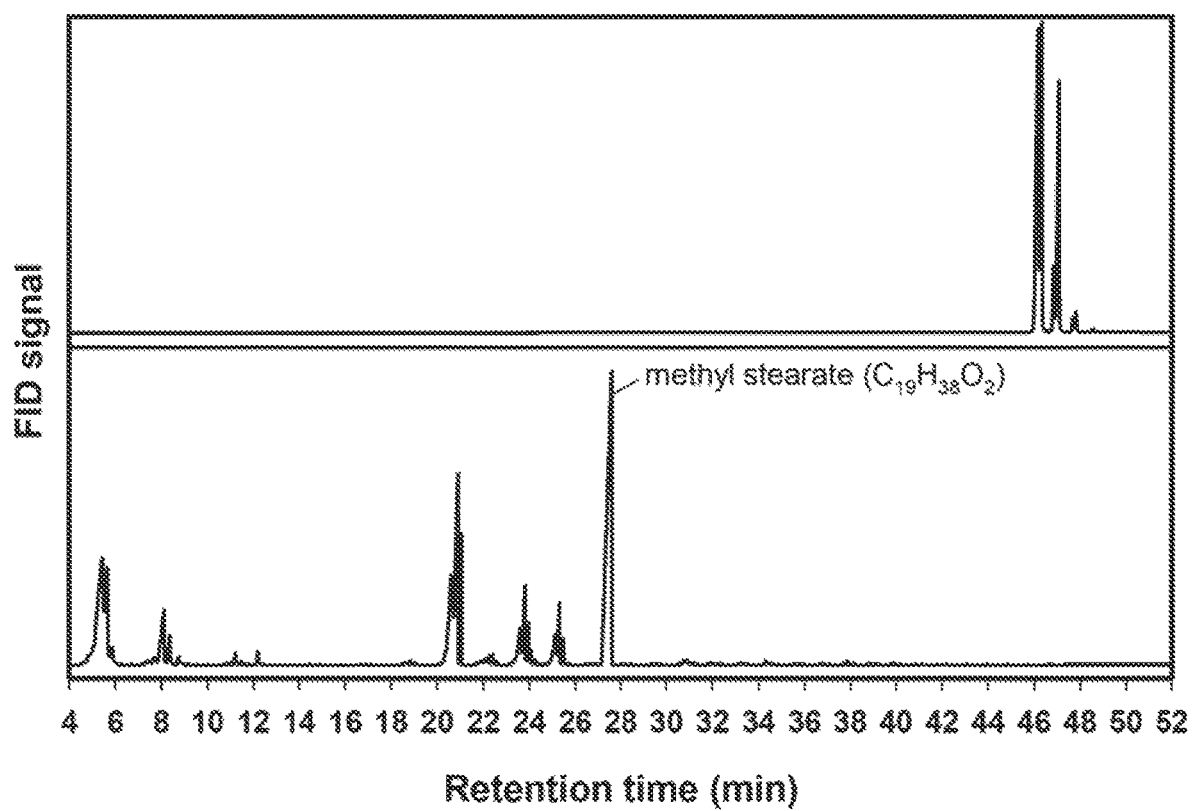
FIG. 4 shows GC-FID chromatograms for starting alkenones 9 (*a*) and butenolysis products 12 (*b*) obtained by reaction 11 with cis-butene and catalyst Ru-HG for 1 h (Entry 6, FIG. 15) showing complete consumption of the alkenones 9. For those reactions giving incomplete conversion, undissolved alkenones 9 could be observed in the reaction mixture (inset).

Proton NMR was not very effective for monitoring the alkenone butenolysis reactions as the spectra for the starting alkenones and butenolysis product mixture were essentially identical. By GC-FID, however, it was clear that no alkenones remained for those reactions with 100% conversion (FIG. 4). What was perhaps equally diagnostic was the dramatic change in reaction appearance upon successful butenolysis. At the start of the reaction the alkenones appear completely insoluble. After conversion to butenolysis products using Ru-II or Ru-HG the mixture becomes homogenous as an indication of high conversion.

Figure 5:
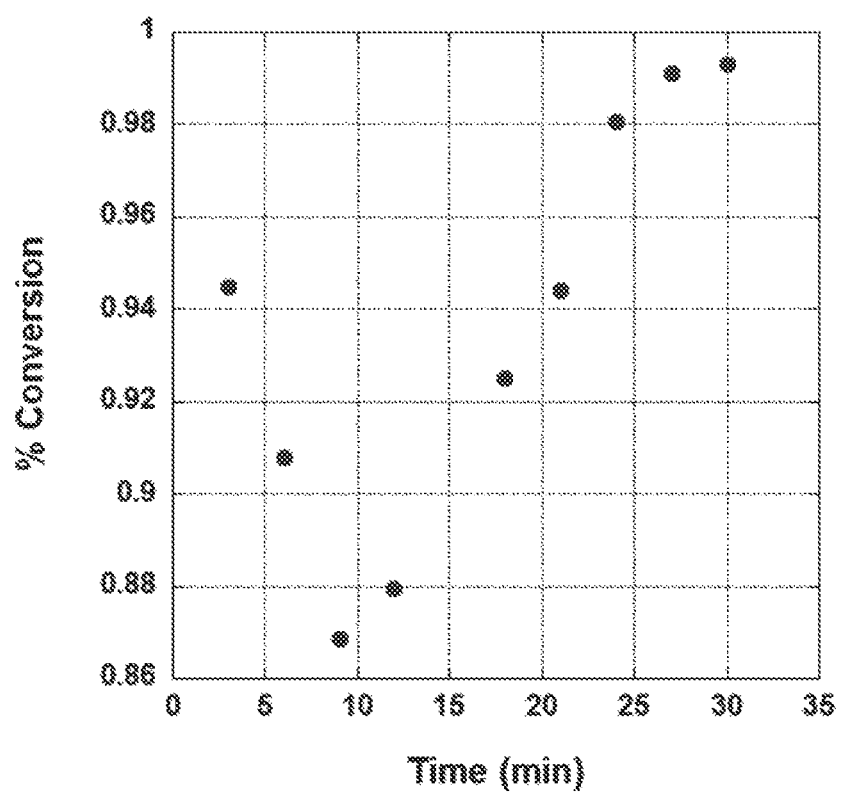
FIG. 5 shows results from butenolysis kinetic experiments by analyzing aliquots from a single reaction with percent conversions normalized to the GC-FID peak area of methyl stearate as an inert internal standard. The apparent decrease during the first 10 minutes is due to initial alkenone solvation.

To better understand the kinetics of the alkenone butenolysis, we attempted to monitor the progress of the reaction using the standard method employed by Patel and coworkers for their butenolysis of methyl oleate. Namely, aliquots were removed from the reaction mixture via syringe that were then quenched by the addition of ethyl vinyl ether and analyzed by GC-FID. Results from this experiment are presented in FIG. 5 where percent conversion was calculated by comparing the GC-FID area ratio of alkenones to methyl stearate as an inert internal standard pre- and post-butenolysis. The kinetics of the reaction were unexpected, showing an apparent decrease in alkenone conversion during the first 10 minutes. We interpret these results to represent a dynamic system of alkenone solvation and butenolysis. Initially, alkenone concentration in the solvent sampled is low due to poor solubility. Over time, dissolved alkenone concentration increases resulting in a lower calculated percent conversion. After 10 minutes the rate of butenolysis appears to exceed the rate of alkenone solvation and the calculated percent conversion increases.

To obtain accurate rate data, it was therefore necessary to perform multiple separate butenolysis reactions quenched at different time increments. Entries 8-17 in FIG. 15 therefore represent results from individual reactions followed by analysis of the entire reaction mixtures. Several interesting observations were made during the course of this somewhat laborious process. As expected, catalyst Ru-HG outperformed catalyst Ru—I, with only 16.7% conversion recorded for Ru—I after six hours (Entry 12). The reaction with Ru-HG was exceptionally fast, giving greater than 90% conversion after only 20 minutes and essentially complete conversion within 30 minutes (Entries 9 and 10). These values are very similar to those reported by Patel and coworkers for the butenolysis of methyl oleate despite the structural differences noted earlier between the alkenones and this FAME. The reaction with trans-2-butene gave significantly lower conversion at the 15-minute mark (Entry 16), perhaps the result of a more rapid initiation of cis-2-butene by the parent catalyst, but after 30 minutes still gave >95% conversion (Entry 17). DCM was chosen as a solvent for these reactions as it had demonstrated the greatest alkenone solubility, although its use is undesirable for any "green" process. We therefore examined the reaction in toluene (PhMe), a more tolerated solvent that showed some alkenone solubility and is often used in olefin metathesis reactions. Reactions performed in toluene gave lower conversions at both 10 and 20 minutes when compared to those in DCM (Entries 8 and 9 vs 13 and 14), likely a reflection of diminished alkenone solubility. Nonetheless, the butenolysis in toluene was still very efficient giving comparable conversion (98%) after 30 minutes at 0° C. (Entry 15).

FIG. 13 shows the expected products from complete butenolysis of the major alkenone (methyl 37:3) constituent isolated from *Isochrysis*. The true product mixture from our butenolysis reactions is of course much more complex because we started not just with pure C37:3 methyl alkenone, but the complete set of alkenones extracted from the biomass that ranged from 37-39 carbons with 2-3 double bonds and methyl or ethyl ketones. Add to this the potential for incomplete butenolysis products along with cis- and trans-isomers and the mixture becomes quite complex. For this reason, GC×GC was used to analyze select butenolysis reactions. GC×GC has been increasingly applied in hydrocarbon analysis, petroleum research, and oil spill science as it has many advantages over one-dimensional GC: its higher chromatographic resolution increases the signal to noise ratio and compounds are separated based on two physical properties (e.g. vapor pressure and polarity depending on choice of column stationary phase), leading to a grouping of chemical classes in a GC×GC chromatogram. Coupling of GC×GC with a flame ionization detector (FID) allows for the quantification of numerous unidentified compounds because most hydrocarbons have similar response factors. Coupled to a time of flight mass spectrometer (TOF-MS), the enhanced resolution and increased signal to noise afforded by GC×GC allows for more accurate spectral identification of many compounds.

Specific alkenones in our samples were identified by their mass spectrum, comparison to published elution order on gas chromatographic columns, textbook descriptions of alkenones, and other more recent studies detailing alkenone structure analysis. Relative amounts of individual alkenones were determined by GC-FID and these values correlated well with those previously reported for the same *Isochrysis* strain used in our study (FIG. 16). Based upon this alkenone profile, we can then predict the products from our butenolysis reaction. For instance, each of the 37 and 38 alkenones should produce 2-heptadecene (2) and two equivalents of 2,9-undecadiene (3) (ref. FIG. 13). Butenolysis of the 37 and 39 alkenones would similarly give 3 along with 8-decen-2-one (1). Considering the relative alkenone percentages, this would then give the distribution outlined in FIG. 16 with 1, 2, and 3 accounting for 83% of the products.

Figure 6:
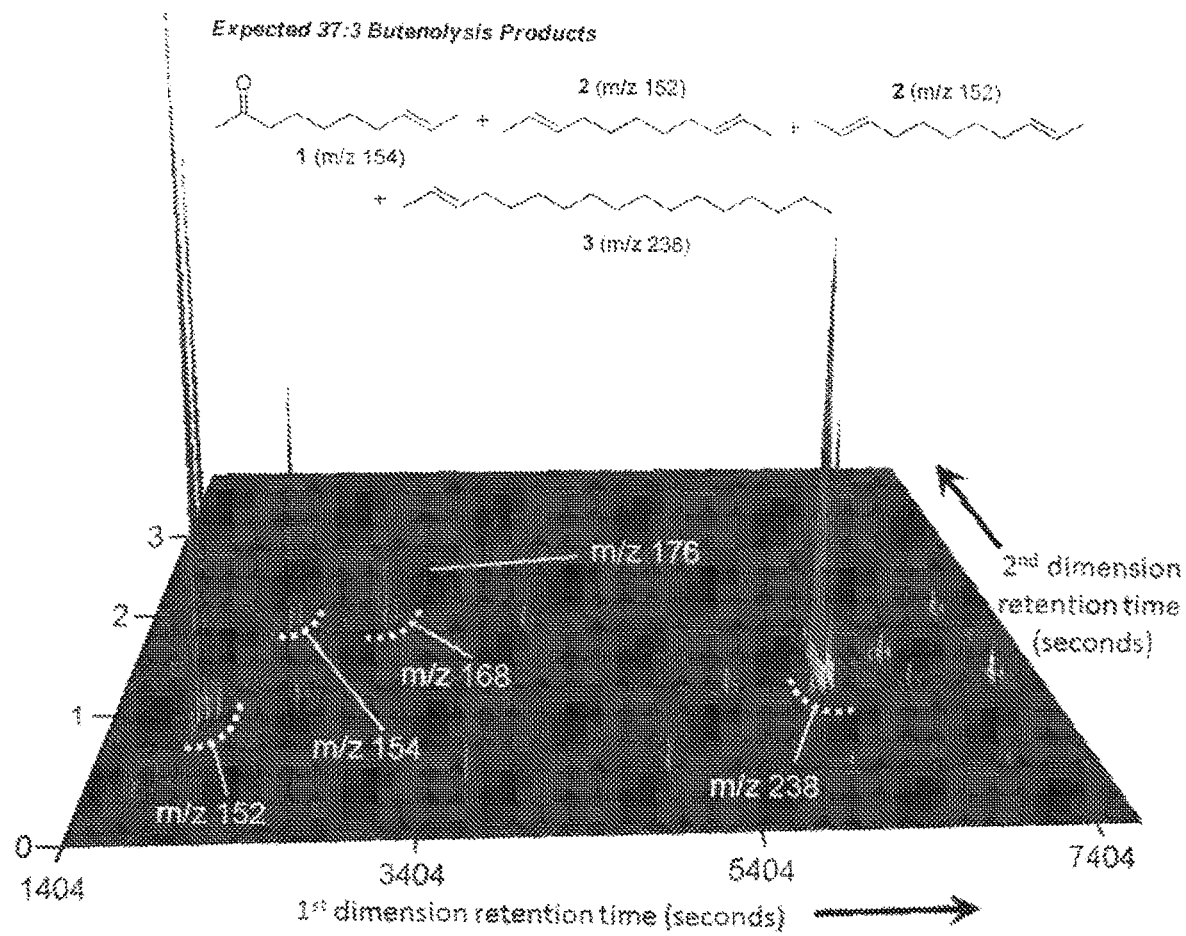
FIG. 6 shows a GC×GC-FID chromatogram of the alkenone butenolysis product mixture 12 obtained after 30 min using cis-2-butene and catalyst Ru-HG. Molecular ion identifications were made by analyzing equivalent peaks in the GC×GC-TOF chromatogram. Note the exceptional resolution allowing for identification and quantification of E,Z-isomers.

FIG. 6 is a typical GC×GC-FID chromatogram of the butenolysis products obtained by reaction of our alkenone mixture with cis-2-butene using catalyst Ru-HG. For reaction times down to 30 minutes in DCM at 0° C., the butenolysis was complete (ref Entry 3, FIG. 15). Each of the expected major products 1, 2, and 3 can be clearly identified. Additionally, for both 1 and 3, two peaks are clearly visible with integration ratios from the GC×GC-FID of 3.9:1 that we have assigned as the trans- and cis-isomers respectively. This is based in part on the earlier work from Patel and coworkers who also reported a 4:1 trans: cis ratio for 2-undecene obtained by butenolysis of methyl oleate. Three peaks in our alkenone butenolysis product mixture were identified with m/z=152 in a ratio of 17.9:7.5:1 that have been assigned to the three possible isomers for 2 (E,E-, E,Z- and Z,Z-). Additional signals include cis- and trans-9-undecen-3-one (m/z=168) obtained from the 38:3 ethyl alkenone contained in our sample (ref. FIG. 2) and catalyst-derived 1-isopropoxy-2-(propenyl)benzene (m/z=176).

Figure 7:
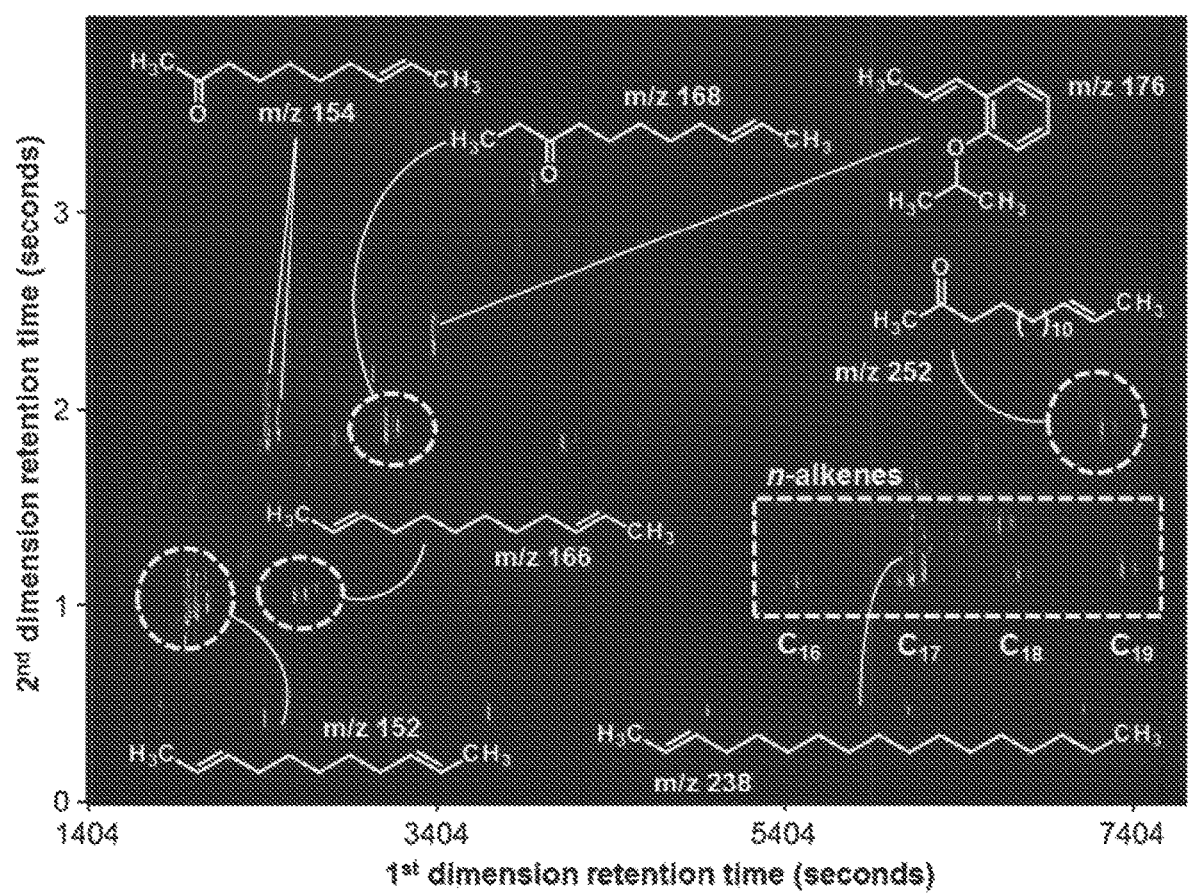
FIG. 7 shows a GC×GC-TOF chromatogram "plan view" of the alkenone butenolysis products mixture 12 showing separation of compounds into different subclasses.

Altogether the ratio of butenolysis products 1:2:3 by GC×GC-FID analysis was typically 1:2.0:2.5 respectively, which is slightly different than what was predicted in FIG. 16 (1:2.3:3.4). Closer inspection of the GC×GC-TOF chromatogram data revealed several unexpected products compared to those presented in FIG. 16 that might help explain this discrepancy (FIG. 7). As is typical of GC×GC data, certain regions of the chromatogram contain different subclasses of compounds. For instance using drilling mud samples containing a series of linear alkenes ("n-alkenes") as a standard reference, an "n-alkene" region could be identified containing not only the expected C17 and C19, but also trace C16 and C18 olefins. For each, two peaks were observed with peak area ratios of approximately 1:4, consistent with our previous cis- and trans-isomer assignments. 2-Octadecene could have arisen from our sample containing very small amounts of a 38-methyl and/or 39-ethyl alkenone. By a similar argument, hexadecene formation could have been formed from a methyl C36 alkenone that we did not detect in our sample nor has a C36 alkenone been reported for *Isochrysis* elsewhere. Alternatively, some double bond isomerization occurred during the course of the cross metathesis which has been reported for metathesis reactions of other aliphatic systems. It is interesting, however, that only C16-C19 alkenes were detected for our butenolysis conducted at both short (e.g. 30 min) and longer (18 h) reaction times rather than the larger range of alkenes that could be envisioned from an isomerization process. Another possibility is that *Isochrysis* biosynthesizes trace amounts of alkenones with differing double bond positions. This would also perhaps explain the peak with m/z=168 in the diene region of the chromatogram that we have tentatively identified as 2,10-dodecadiene. Efforts are ongoing to characterize completely and better understand the mixture of products generated in this and other related reactions as it relates to both product use and alkenone structure elucidation.

Figure 8:
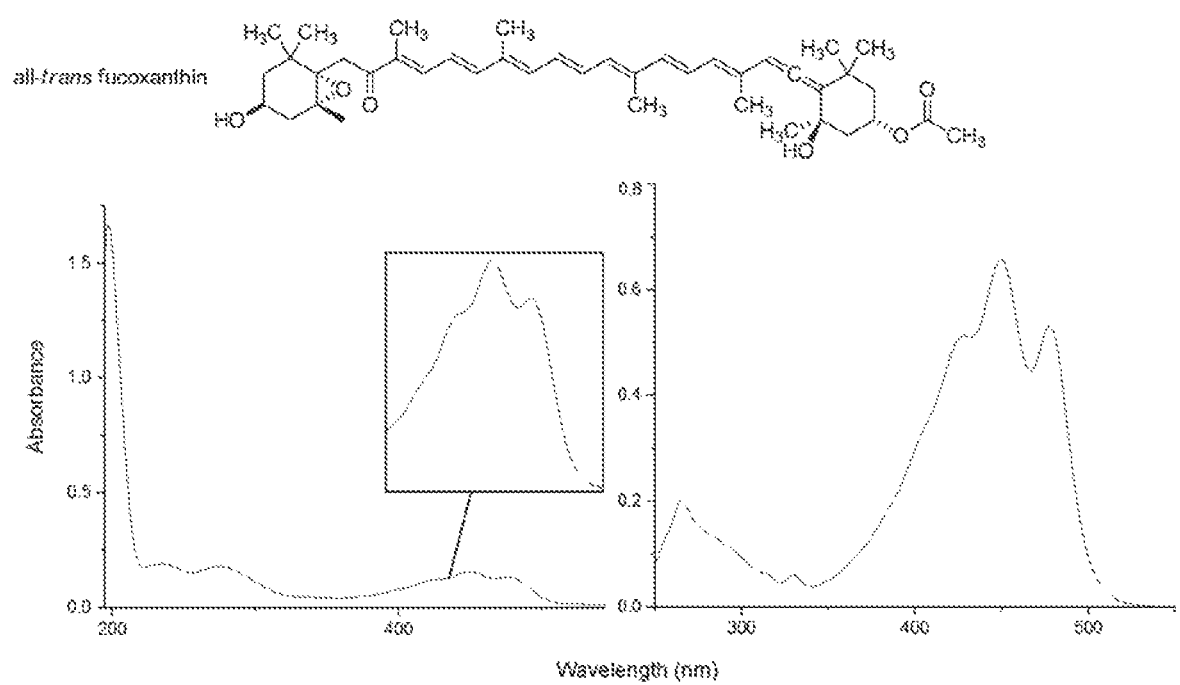
FIG. 8 shows UV absorbance spectra of red fractions 16 obtained by chromatography 15 of the neutral lipids (left) and a fucoxanthin standard solution (right) showing characteristic maxima at 446 and 475.

During the course of isolating and purifying alkenones from this neutral lipid fraction by chromatography on silica, we obtained a few small fractions that appeared as bright red solutions. Recently there have been a few reports describing the isolation and quantification of the carotenoid fucoxanthin from *Isochrysis*. Fucoxanthin is a structurally complex oxidized form of β-carotene (a xanthophyll, FIG. 8) that has received significant interest for its range biological activities including anti-inflammatory, anti-angiogenic, anti-diabetic, anti-obesity, and anti-carcinogenic effects. Indeed, a UV-Vis spectrum of our red fractions showed characteristic peaks at 428, 446 and 475 that were consistent with the spectrum obtained for the fucoxanthin standard and reported elsewhere (FIG. 8).

Interestingly, hexanes had been shown to be a poor solvent for fucoxanthin extraction from algal culture, with alcoholic solvents like ethanol and methanol proving far superior. For instance, in the study by Kim et al., extraction with hexanes produced 1.04 mg of fucoxanthin from 1 g of dry *Isochrysis* culture powder (1.04 mg/g DW) whereas ethanol gave 19.76 mg/g DW under identical conditions. These results suggested that after our hexanes extraction that we ultimately use to make biodiesel, the majority of fucoxanthin remains in what was previously waste biomass and might still be recoverable.

Figure 9:
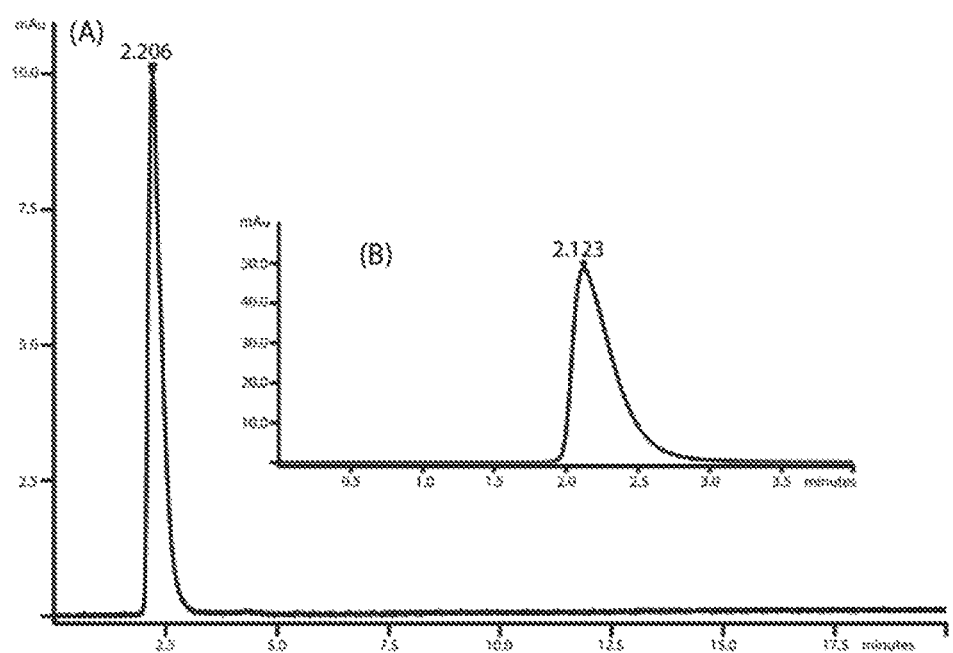
FIG. 9 shows a HPLC chromatogram of the biomass oil 3 (A) and fucoxanthin standard (B, inset).
Figure 10:
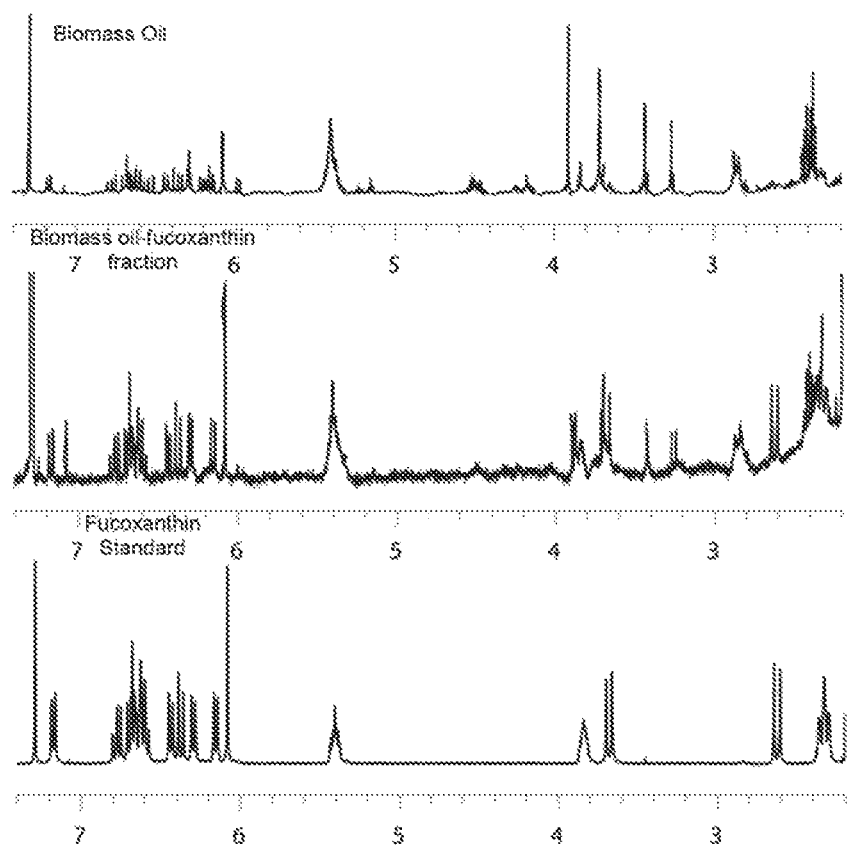
FIG. 10 shows a $^1H$ NMR spectrum (500 MHz CDCl3) of the extracted biomass oil 3 (top), the fucoxanthin fraction 16 obtained from the biomass oil 3 (middle), and the fucoxanthin standard (bottom).

Sequential hexanes/ethanol extraction for the co-production of biodiesel and fucoxanthin. Hexanes extraction of 30 g of dry *Isochrysis* culture was performed as had been previously described and produced 5.85 g biofuel oil, consistent with our prior reports (FIG. 17). The post hexanes-extracted biomass was then removed from the cellulose extraction thimble and submerged in ethanol. Due to the known photolability of fucoxanthin and other carotenes, the ethanol extraction along with all subsequent steps was performed in the dark to minimize exposure to light. The yield of biomass oil after 24 h at room temperature was 7.3% (w/w) and fucoxanthin content was 19% (w/w) compared to only 3% (max.) fucoxanthin content for the biomass oil (FIG. 9). For further confirmation, a fucoxanthin-enriched biomass oil could be obtained by unoptimized chromatography on silica to produce a product (0.54 g from 1.89 g biomass oil) that was now 44% fucoxanthin according to HPLC analysis. The $^1$H NMR spectra for both the biomass oil and this enriched biomass oil showed peaks consistent with that for the fucoxanthin standard (FIG. 10).

Kim and coworkers reported a significant correlation between the duration of ethanol extraction and the amount of fucoxanthin obtained. Specifically, maximum yields were obtained after only 5 minutes at room temperature (20.28 mg/g DW after 5 minutes vs. 17.38 mg/g after 24 h). The authors attribute this difference as being due to the sensitivity of fucoxanthin toward decomposition. To test the impact of time on our own fucoxanthin ethanol extraction, dry *Isochrysis* culture (50.6 g) was again first extracted with n-hexanes in a Soxhlet apparatus. The post-extracted biomass was then split (2×22.5 g), with one half extracted in ethanol for 1 h and the other extracted for 24 h at room temperature. Somewhat surprisingly, the yield of fucoxanthin was substantially higher for the 24 h extraction. This was not a function of one biomass oil being more enriched in fucoxanthin (21.5% and 20.0% for the 24 h and 1 h extractions respectively), but rather the amount of algal oil that was obtained from the different extraction techniques (2.22 g vs. 0.97 g). Kim et al. described the use of dried biomass "powder" for their fucoxanthin extraction study. Additionally, those experiments were conducted on a significantly smaller scale (100 mg vs. 20-30 g dry biomass) which might also contribute to the discrepancy between our extraction time data and theirs. Assuming that the sample had not been split and the entire 45 g of post hexanes-extracted biomass was extracted with ethanol for 24 h to produce 4.44 g (2×2.22 g) biomass oil, this would correspond to 18.8 mg/g DW. Combined with the fucoxanthin contained in the biofuel oil and data obtained from the 30 g biomass extraction, average total fucoxanthin extracted from our *Isochrysis* samples is 21.73 mg/g DW. This value is in the range of the maximum value reported by Kim et al. by extraction with ethyl acetate for 1 h at room temperature (20.98 mg/g DW) as well as the total (sum of E,Z-isomers) fucoxanthin content in *Isochrysis* biomass reported by Crupi and coworkers (19.82±3.72).

On average, 75% of the total extracted fucoxanthin is contained in our biomass oil, which is similar to that obtained by Kim et al. using a complimentary two-phase lipid/fucoxanthin separation procedure. Unlike the two-phase separation procedure, however, our method does not disrupt or alter the biomass-to-biodiesel process. Rather it is the biodiesel waste-stream to which value is being added, not unlike other reports describing the use of residual algal biomass as feed or its gasification to fuel. Yields of *Isochrysis* are estimated to be 175 metric tons of biomass dry weight hectare$^{-1}$ year$^{-1}$ (outdoor pond). At approximately 2% (w/w) fucoxanthin content, this would correspond to 3.5 metric tons of fucoxanthin hectare$^{-1}$ year$^{-1}$. The current market for fucoxanthin is as a dietary supplement using mixtures isolated from several edible brown seaweeds. Given the range of reported biological activities, with increased supply there could also be an increase in its applications resulting in a potentially not-insignificant offsetting of the fuel cost.

There is great interest in the co-production of value added chemicals as a means for improving the economic viability of algal biofuels. By exploiting differences in solvent extraction efficiencies, a tandem biomass extraction protocol has been developed that allows for simultaneous biodiesel production and isolation of a high-value carotenoid fucoxanthin from the marine microalgae *Isochrysis*. Specifically, extraction of dry *Isochrysis* biomass with hexanes using a Soxhlet apparatus provides acylglycerols that can then be converted to biodiesel by means of a transesterification reaction. That same residual biomass can then be extracted with ethanol to provide an algal oil enriched in fucoxanthin (20% w/w). Quantification of the amount of fucoxanthin in the ethanol algal oil revealed that this sequential extraction is quite selective and with total values near the maximum found in other reports describing fucoxanthin from *Isochrysis*. Efforts are ongoing to optimize and analyze this procedure as a general strategy for the co-production of fuel and value-added compounds from *Isochrysis* and other promising algae feed-stocks.

Example 3

This example demonstrates the co-purification, from a single batch of algae, of an alkenone-enriched sample in conjunction with an other commercially valuable second molecule (e.g. therapeutic molecule, neutraceutical, fuel, food-stuff, raw material, etc.).

The co-production of alkenones and alkenone derivatives from what in many instances is the waste-stream of a second commercially valuable product may significantly increase the commercial attractiveness of alkenone extraction because the cost of culture, growth, and preparation may be considered as being born by the production of the second product. Furthermore, in the production of biodiesel (e.g. FAMEs) and biofuels, a significant portion of algal biomass (often containing alkenones), is discarded as the waste-stream.

In this example, both FAMEs and a commercially valuable second molecule (e.g. fucoxanthin, astaxanthin, beta-carotene, and other carotenoids) are produced, and an alkenone-enriched fraction is obtained as well.

2. Microalgal Species and Sample Preparation.

The marine microalgae *Isochrysis* sp. "T-iso" is used in the present example although *Isochrysis* sp. "C-iso" is also suitable as well as any other suitable such algae species described herein. The algae are grown in greenhouse ponds under natural sunlight in a modified F/2 media. Average water temperatures are 18° C. to 20° C. A sample of algal wet biomass is harvested and then lyophilized to yield dry *Isochrysis* algal culture 1. In some embodiments, the algal culture 1 is not dried prior to solvent extraction.

2. Extraction of the Algal Culture.

The *Isochrysis* algal culture is mixed with one or more liquids to produce a two-phase system. In the first instance (e.g. dry *Isochrysis* and a polar solvent such as n-hexanes), the two-phase system comprises a solid and a liquid. In the second instance, a liquid two-phase system is produced comprising a first polar phase and a second less polar phase. In either instance, after they are produced, the two phases are separated by the appropriate methods as is known to the art, yielding an alkenone-enriched phase (i.e. a sample comprising alkenones, lipids, fatty acids, etc., biofuel oil) and a second phase enriched with the other commercially valuable product or molecule.

In some embodiments of this example, one or more liquids are added to the algae from a group comprising alkanes, alkenes, alkynes, alcohols, ketones, amines, amides, esters, ethers, acids, organic compounds, carboxylates, halogenated hydrocarbons, surfactants, detergents, polar solvents, water, ethanol, methanol, butanol, alcohols, n-hexanes, chloroform, dichloromethane, chloromethane, dichloroethane, tetrahydrofuran, methyltetrahydrofuran, acetonitrile, nitromethane, propylene carbonate, acetone, and liquid hydrocarbons. In a specific embodiment of the example, water, a polar solvent (e.g. ethanol, methanol), and n-hexanes are added to extract the dry culture. In another embodiment, water, an alcohol (e.g. ethanol, methanol, butanol), and chloroform are added. In yet another embodiment, water, a polar solvent, and a liquid hydrocarbon are added to the extraction. In one case where a wet (i.e. aqueous) algal culture is used, a polar solvent and n-hexanes are used. In another case where a wet algal culture is extracted, a polar solvent and chloroform are added.

Once the two phases are separated, the alkenone-enriched phase (e.g. biofuel oil in the case of dry algae extracted with a non-polar solvent or the lower polarity phase in the case of algae extracted with ethanol, water, and n-hexanes) is further purified.

In one embodiment, a Soxhlet extraction apparatus or similar device is utilized for the extraction. Additionally, in some embodiments, care may be taken at this stage to ensure that the samples and subsequent materials are exposed to a minimal amount of light.

3. Isolation of Fatty Acids and Lipids from the Alkenone-Enriched Sample.

After the algae extraction and phase separation, the alkenone-enriched sample (e.g. sample comprising the biofuel oil) is processed in an esterification reaction to produce fatty acid methyl esters (i.e. FAMEs) from fatty acids present in the sample. The FAMEs are then separated from the sample (e.g. In one embodiment, this is accomplished by treating the sample with KOH at 60° C. for 3 hours; the resulting saponified acylglycerols are selectively partitioned into water while the neutral lipids are extracted with n-hexanes. Reacidification of the aqueous phase with HCl and extraction with n-hexanes may produce the free fatty acids (FFAs). Alkenones are further derivatized and/or purified and/or analyzed as described in Example 2 and elsewhere herein.

All publications patents and published patent applications referred to in this application are specifically incorporated by reference in their entirety as if each individual publication, patent or published patent application was specifically and individually indicated to be incorporated by reference. In case of conflict, the present application, including its specific definitions herein, will control. Incorporated references include Lindell et al. U.S. Publication No. US2014-0171608A1 and Bidle et al. U.S. Pat. No. 8,557,514.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of isolating at least one product from algae, the method comprising:
   (a) growing an algal mariculture capable of producing alkenones;
   (b) extracting the algal mariculture with a non-polar liquid solvent to produce an extraction mixture;
   (c) separating the extraction mixture into at least a first fraction and a second fraction, wherein the first fraction is a lipid-containing mixture including alkenones and less than 50% (w/v) fatty acid methyl esters (FAMEs); and
   (d) isolating a mixture of alkenones, lipids, and FAMEs from the first fraction.

2. The method of claim 1, further comprising the step of isolating alkenones from said mixture of alkenones, lipids, and FAMEs.

3. The method of claim 1, wherein the algal mariculture comprises an algal family selected from one or more of the *Isochrysis* family, the *Emiliania* family, and the *Gephyrocapsa* family.

4. The method of claim 1, wherein the non-polar solvent contains no fatty acids or fatty acid derivatives.

5. The method of claim 1, wherein the algal mariculture contains at least 5% alkenones (w/w) relative to the starting dry weight of the algal mariculture.

6. The method of claim 1, further comprising the step of dehydrating the algal mariculture.

7. The method of claim 6, wherein the dehydration is performed by one or more methods consisting of lyophilization, evaporation with or without the addition of solvents, vacuum drying, drum drying, hot air exposure, dielectric drying, supercritical drying, and natural air drying, or a combination thereof.

8. The method of claim 1, further comprising the step of isolating alkenones from the first fraction by combining the first fraction with a polar solvent or a partially polar solvent selected from one or more of chloromethane, dichloromethane, dichloroethane, tetrahydrofuran, dimethylformamide, acetonitrile, nitromethane, propylene, carbonate, formic acid, butanol, isopropanol, methyltetrahydrofuran, trifluoromethylbenzene, ethyl acetate, ethyl ether, acetone, dimethyl sulfoxide, alcohols, acetic acid, esters, or ethers.

9. The method of claim 8, wherein the separation with the polar solvent or partially polar solvent produces a third fraction comprising neutral lipids.

10. The method of claim 1, further comprising the step of isolating a mixture of alkenones and lipids from said mixture of alkenones, lipids, and FAMEs.

11. The method of claim 2, wherein the isolated alkenones are recrystallized in a second solvent.

12. The method of claim 1, further comprising the step of isolating a co-product from the second fraction.

13. The method of claim 12, wherein said co-product from second fraction is a carotenoid.

14. The method of claim 12, wherein said co-product from second fraction is a pigment.

15. The method of claim 14, wherein said co-product from second fraction is fucoxanthin.

16. The method of claim 1, further comprising the step of isolating a co-product from the first fraction.

17. The method of claim 16, wherein said co-product is an acylglycerol.

* * * * *